(12) United States Patent
Marterer et al.

(10) Patent No.: US 9,365,565 B2
(45) Date of Patent: Jun. 14, 2016

(54) SALTS OF AZA-BICYCLIC DI-ARYL ETHERS AND PHARMACEUTICALS THEREOF

(75) Inventors: Wolfgang Marterer, Basel (CH); Mahavir Prashad, East Hanover, NJ (US); Edwin Bernard Villhauer, East Hanover, NJ (US); Liladhar Murlidhar Waykole, East Hanover, NJ (US); James Anthony Vivelo, Basking Ridge, NJ (US); Bertrand Sutter, Basel (CH); Jean-Claude Bianchi, Basel (CH); Raeann Wu, East Hanover, NJ (US); Denis Har, East Hanover, NJ (US); Piotr H. Karpinski, East Hanover, NJ (US); Massimo Pignone, Basel (CH); Doris Stingelin, Basel (CH); Eckart Buerger, Köniz (CH)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 14/232,717

(22) PCT Filed: Jul. 12, 2012

(86) PCT No.: PCT/EP2012/063712
§ 371 (c)(1),
(2), (4) Date: Mar. 28, 2014

(87) PCT Pub. No.: WO2013/010916
PCT Pub. Date: Jan. 24, 2013

(65) Prior Publication Data
US 2014/0220125 A1 Aug. 7, 2014

Related U.S. Application Data

(60) Provisional application No. 61/508,147, filed on Jul. 15, 2011.

(51) Int. Cl.
*A61K 9/20* (2006.01)
*C07D 453/02* (2006.01)
(Continued)

(52) U.S. Cl.
CPC ............ *C07D 453/02* (2013.01); *A61K 9/2054* (2013.01); *A61K 31/194* (2013.01);
(Continued)

(58) Field of Classification Search
CPC .................................................... A61K 9/2054
See application file for complete search history.

(56) References Cited

U.S. PATENT DOCUMENTS

2003/0220340 A1 11/2003 Roberts et al.

FOREIGN PATENT DOCUMENTS

WO WO 01/60821 A1 8/2001
WO 2004022556 A1 * 3/2004
(Continued)

OTHER PUBLICATIONS

Blagden et al., "Crystal engineering of active pharmaceutical ingredients to improve solubility and dissolution rates," Advanced Drug Delivery Reviews. 59:617-30 (2007).
(Continued)

*Primary Examiner* — Carlos Azpuru
(74) *Attorney, Agent, or Firm* — Hoffman Warnick LLC

(57) ABSTRACT

The present invention relates to salts of (R)-3-(6-(4-methylphenyl)-pyridin-3-yloxy)-1-aza-bicyclo[2.2.2]octane, to methods for making them or their precursors, to pharmaceutical compositions comprising them, and to their use as medicaments.

16 Claims, 11 Drawing Sheets

(51) Int. Cl.
| | |
|---|---|
| A61K 31/194 | (2006.01) |
| A61K 31/439 | (2006.01) |
| C07C 55/08 | (2006.01) |
| C07C 55/10 | (2006.01) |
| C07C 57/145 | (2006.01) |
| C07C 57/15 | (2006.01) |

(52) U.S. Cl.
CPC ............... *A61K31/439* (2013.01); *C07C 55/08* (2013.01); *C07C 55/10* (2013.01); *C07C 57/145* (2013.01); *C07C 57/15* (2013.01); *A61K 2300/00* (2013.01)

(56) References Cited

FOREIGN PATENT DOCUMENTS

| WO | WO 2004/022556 A1 | 3/2004 |
|---|---|---|
| WO | 2006005608 A1 | 1/2006 |
| WO | 2011009890 A2 | 1/2011 |

OTHER PUBLICATIONS

English translation of Office Action for Columbia Patent Application No. 14-007.836, date of issuance of Office Action: Feb. 17, 2015, date of English translation: Apr. 14, 2015, (7 pages).

Lena Ohannesian and Anthony J. Streeter, Handbook of Pharmaceutical Analysis, New York: Marcel Dekker, 2002, Chapters 1 and 2.

Raymond C. Rowe, Paul J. Sheskey, Walter G. Cook, and Marian E. Fention, Handbook of Pharmaceutical Expineints, 6th ed. London: Pharmaceutical Press, 2003, pp. 120, 132, 188, 211, 385-398, and 705-734.

International Search Report, Appl. No. PCT/EP2012/063712, Sep. 27, 2012, 3 pgs.

Bodnar et al., "Discovery and structure-activity relationship of quinuclidine benzamides as agonists of alpha7 nicotinic acetylcholine receptors," J Med Chem. 48(4):905-8 (2005). Abstract provided.

Grady et al., "Structural differences determine the relative selectivity of nicotinic compounds for native alpha 4 beta 2*-,alpha 6 beta 2*-, alpha 3 beta 4*—and alpha 7-nicotine acetylcholine receptors," Neuropharmacology. 58(7):1054-66 (2010). Abstract and Author Manuscript provided.

First Office Action for Chinese Patent Application No. 201280035085.6, dated Feb. 2, 2015, (12 pages).

"A 4-week, parallel-group, randomized, double-blind, placebo-controlled, adaptive proof of concept study of AQW051 at up to three dose levels for the treatment of patients with findings consistent with mild Alzheimer's disease (AD) or Mild Cognitive Impairment (amnestic MCI)," EU Clinical Trial Register, EudraCT Number: 2007-001846-42, Novartis Pharma AG. Printed on Jan. 13, 2016.

"A multi-centre, randomized, double-blind, placebo-controlled, parallel-group, multiple oral dose study to assess the efficacy, safety and tolerability of AQW051 in reducing L-dopa induced dyskinesias in Parkinson's patients with moderate to severe L-dopa induced dyskinesias," EU Clinical Trial Register, EudraCT Number: 2011-001092-39, Novartis Pharma Services AG. Printed on Jan. 13, 2016.

Decision of Rejection for Japanese Patent Application No. 2014-519458, dated Jan. 5, 2016, 4 pages.

"A multi-centre, randomized, double-blind, placebo-controlled, parallel-group, multiple oral dose study to assess the efficacy, safety and tolerability of AQW051 in reducing l-dopa induced dyskinesias in Parkinson's patients with moderate to severe L-dopa induced dyskinesias," EU Clinical Trial Register, EudraCT Number: 2011-001092-39, Novartis Pharma Services AG. Printed on Dec. 5, 2011.

Ibrahimi et al., "C-versus O-Arylation of an Enol-Lactone Using Potassium tertbutoxide," Int. J. Mol. Sci. 4:371-8 (2003).

Second Examination Report for CO Application No. 14007836, dated Jan. 19, 2016, 34 pages.

Decision of the Intellectual Property Office for TW Application No. 101101542, dated Jan. 28, 2016, 9 pages.

\* cited by examiner

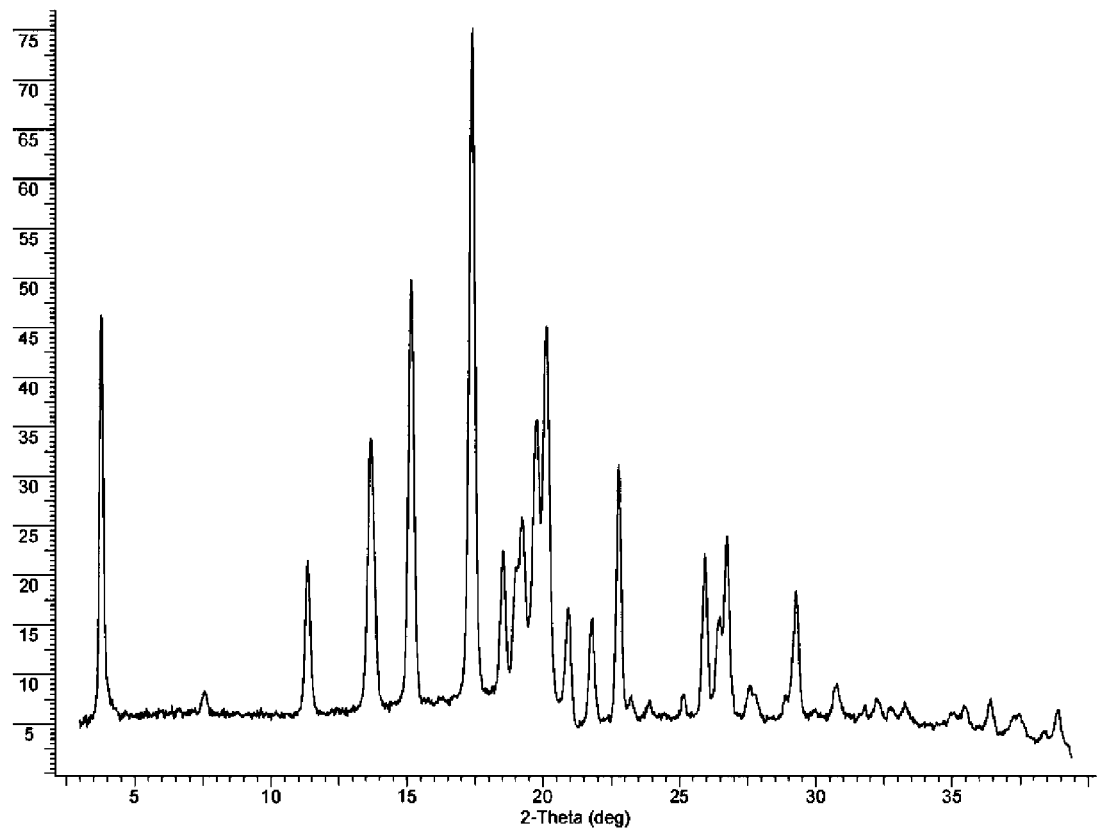
Figure 1: Fumarate

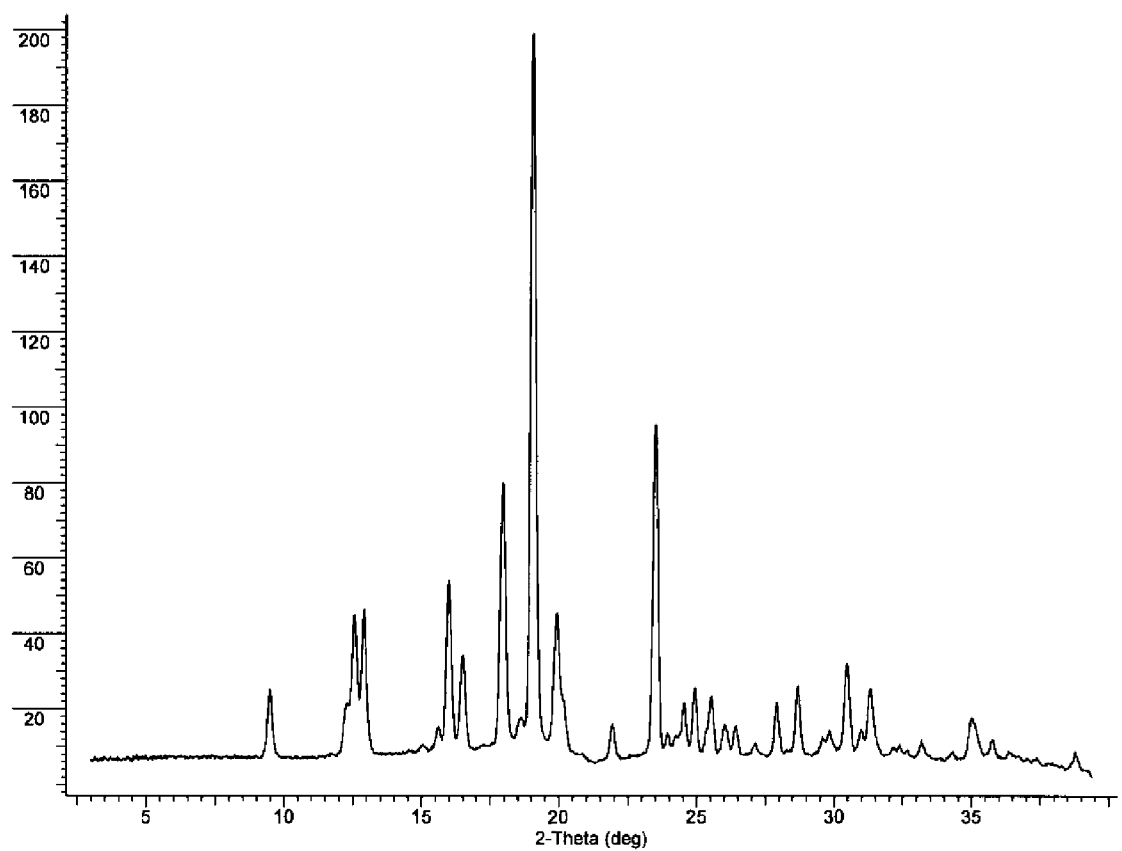
Figure 2: Maleate

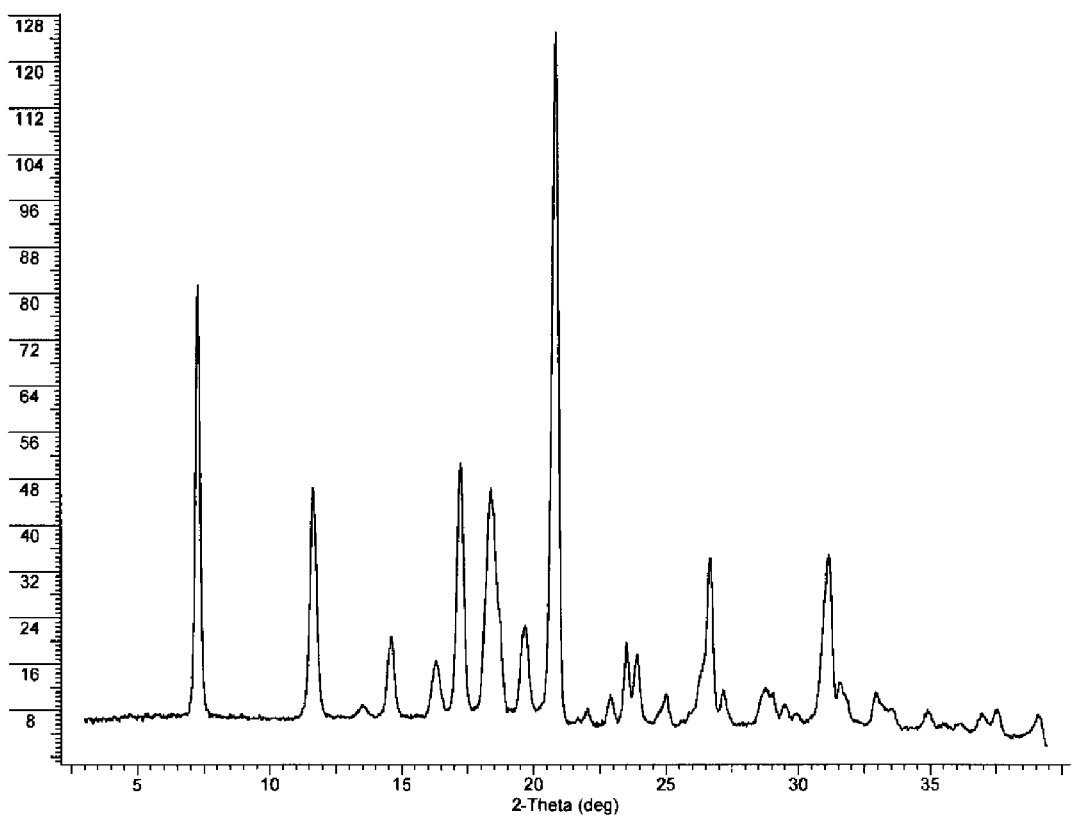
Figure 3: Hydrochloride

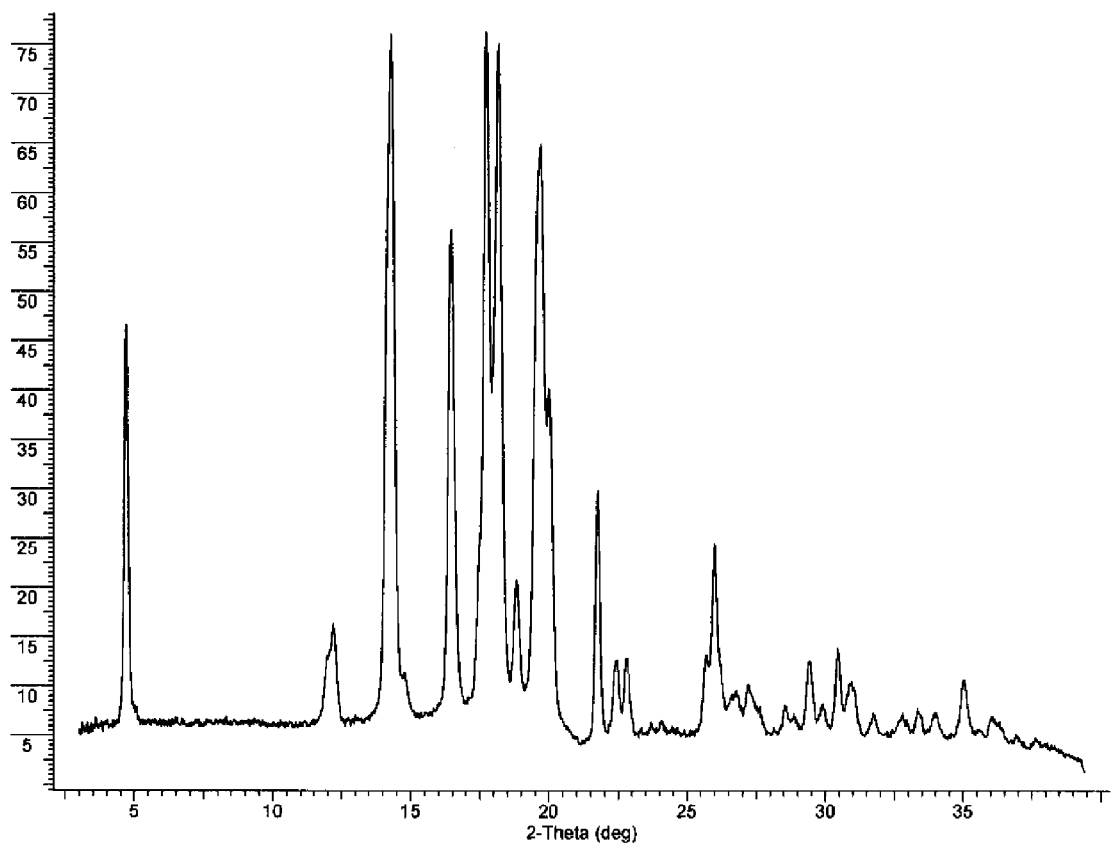
Figure 4A: Phosphate, Form A

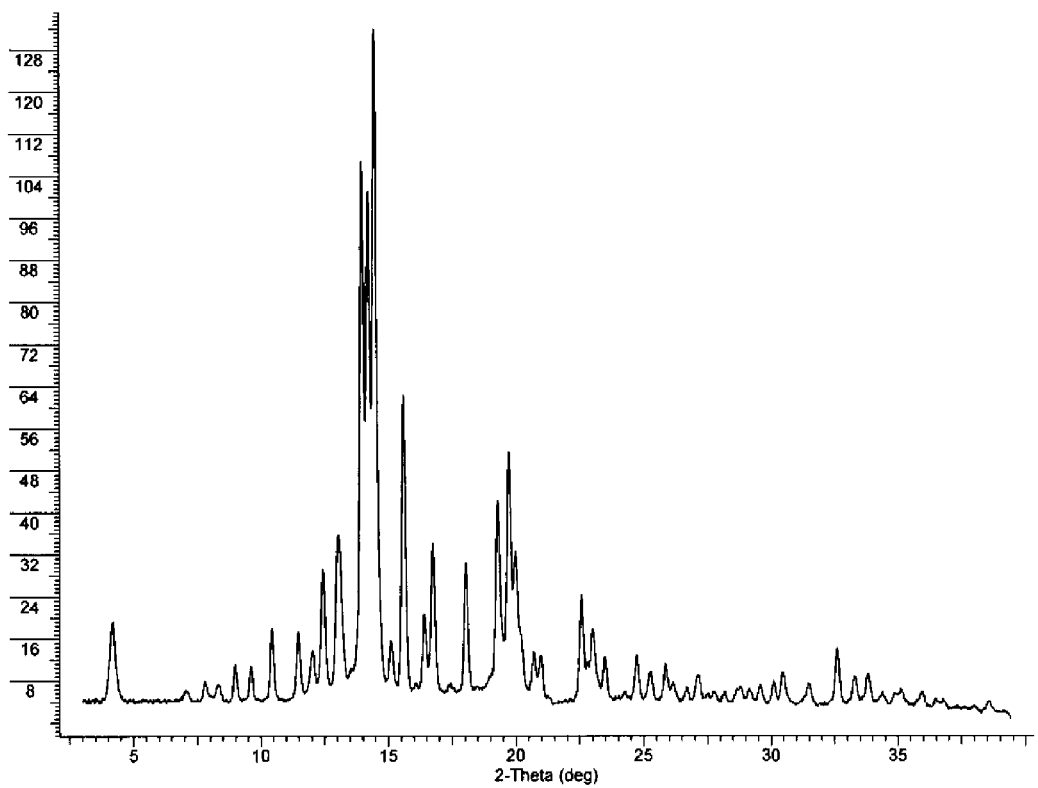
Figure 4B: Phosphate, Form B

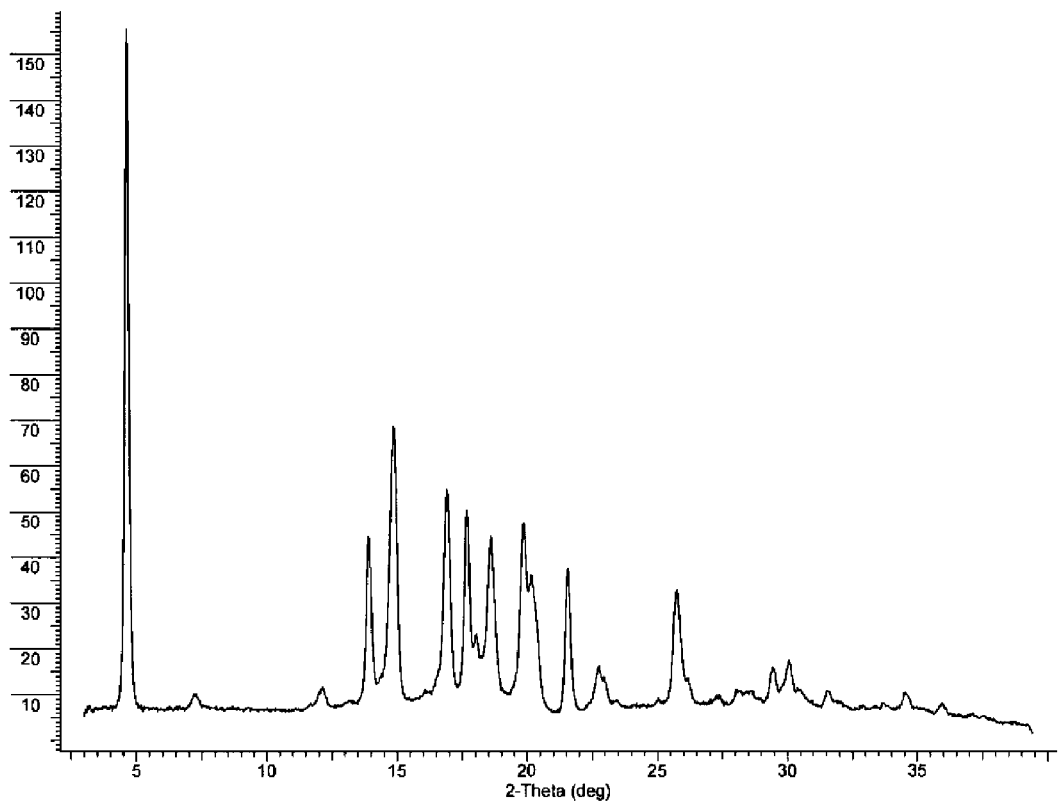

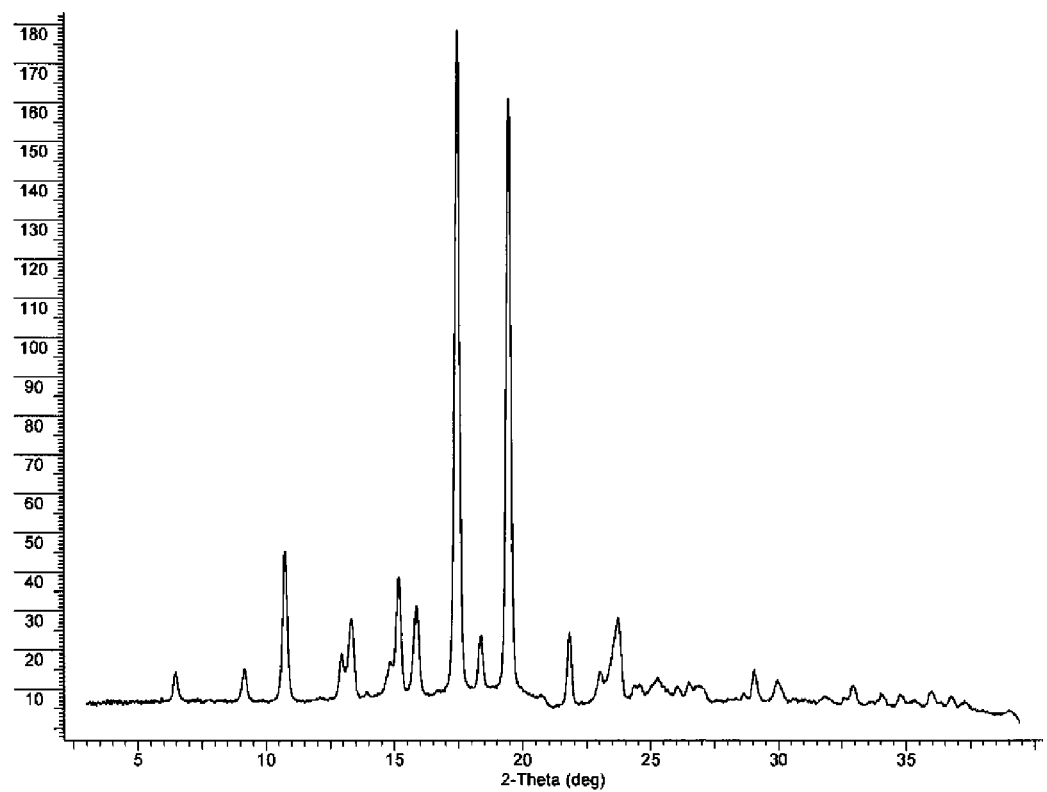

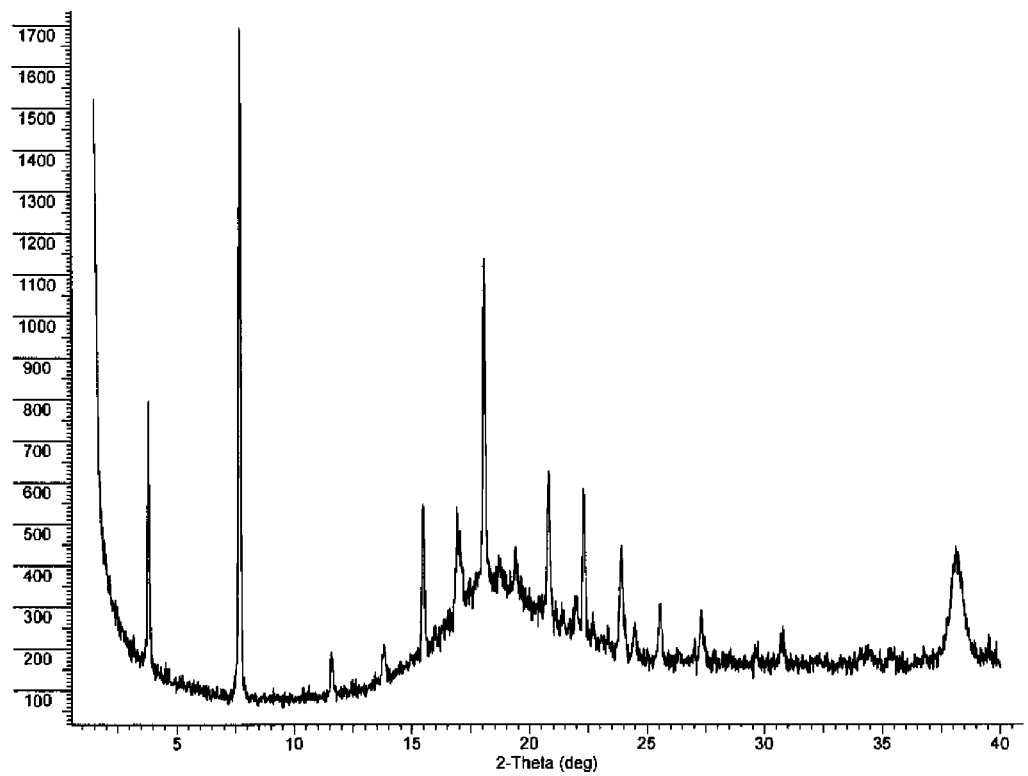
Figure 5B: Succinate, Form B

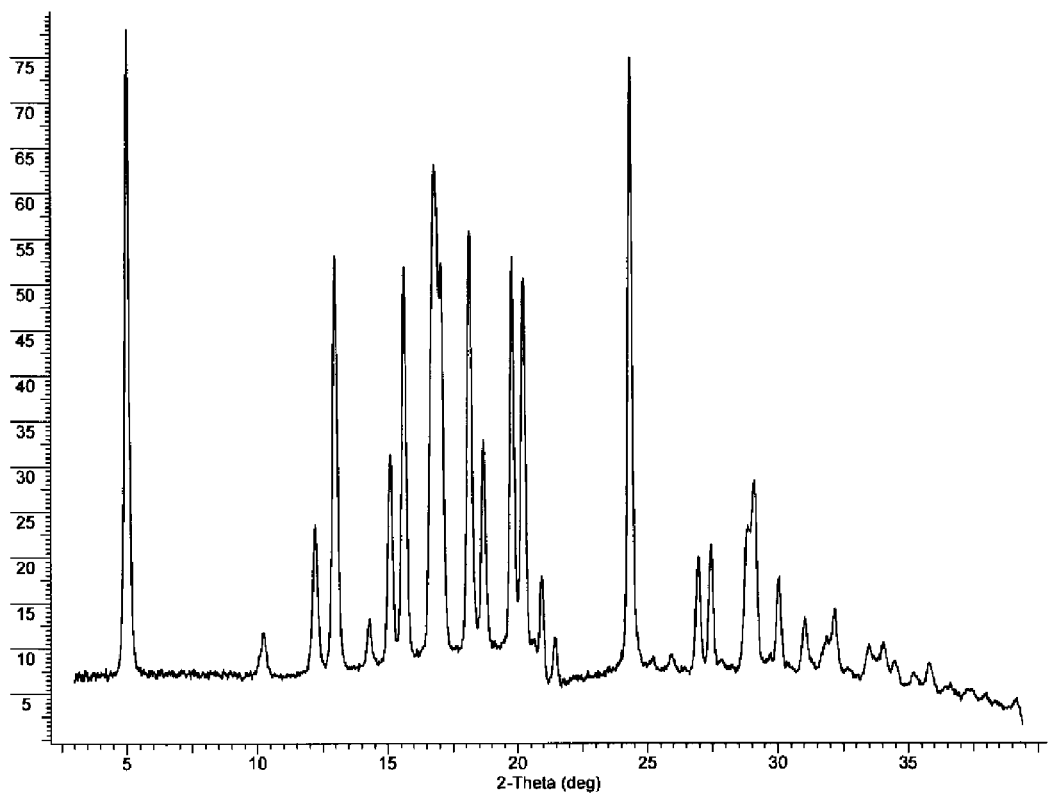
Figure 6: Malonate

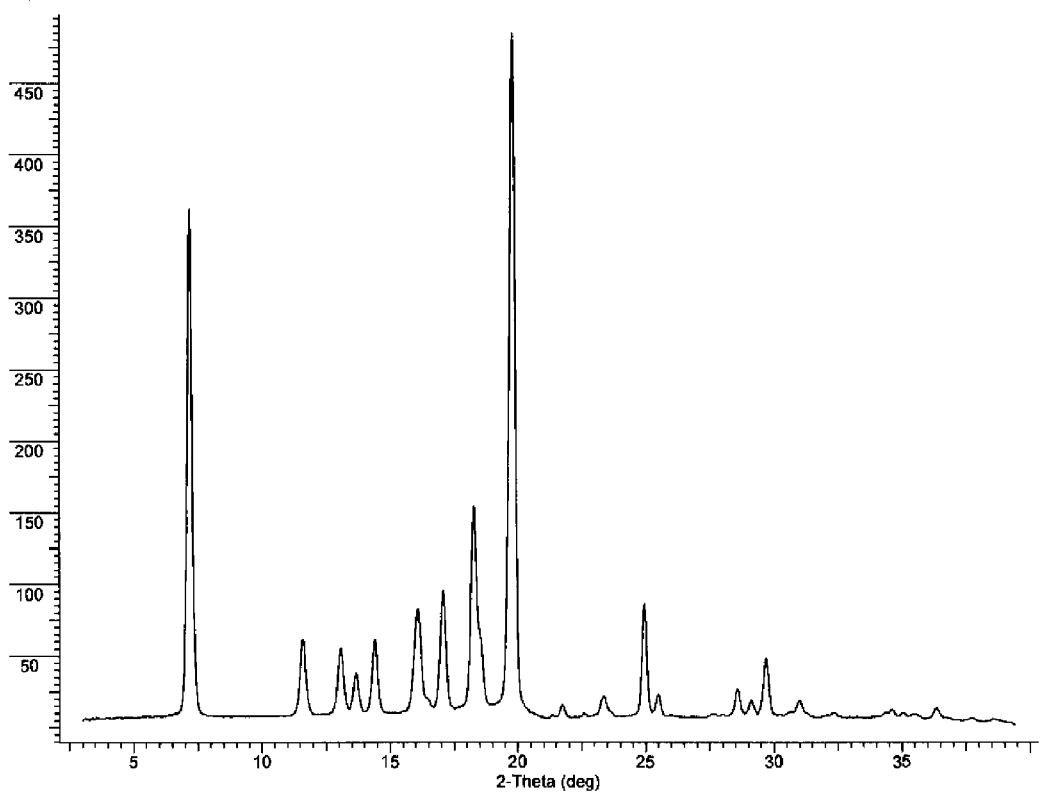
Figure 7A: Free base, Form A

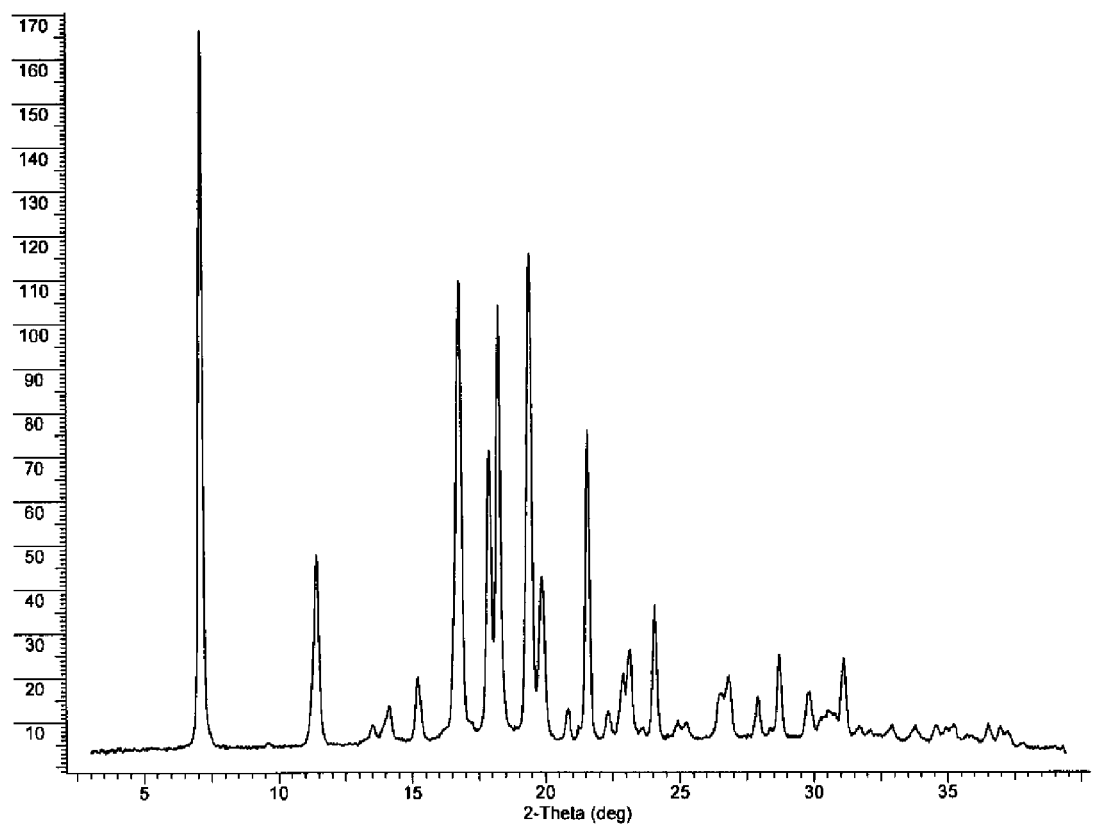
Figure 7B: Free base, Form B

SALTS OF AZA-BICYCLIC DI-ARYL ETHERS AND PHARMACEUTICALS THEREOF

CROSS-REFERENCE TO RELATED PATENT APPLICATIONS

This application is a National Stage of International Application No. PCT/EP2012/063712, filed Jul. 12, 2012, which is based upon and claims the benefit of priority from prior U.S. Provisional Patent Application No. 61/508,147, filed Jul. 15, 2011, the entire contents of all of which are incorporated herein by reference in their entirety.

The present invention relates to salts of (R)-3-(6-(4-methylphenyl)-pyridin-3-yloxy)-1-aza-bicyclo[2.2.2]octane, to methods for making them or their precursors, to pharmaceutical compositions comprising them, and to their use as medicaments.

I. Salts of Aza-Bicyclic Di-Aryl Ethers

The compound (R)-3-(6-(4-methylphenyl)-pyridin-3-yloxy)-1-aza-bicyclo[2.2.2]octane of the formula I

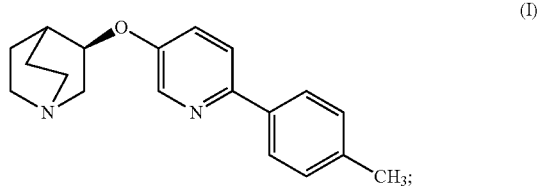 [SMILES: Cc1ccc(-c2ccc(O[C@H]3CN4CCC3CC4)cn2)cc1]

is described in WO2004/022556A1. Valuable pharmacological properties are attributed to this compound; thus it can be used as a nicotinic acetylcholine receptor alpha 7 agonist (α7-nAChR agonist) useful in therapy for disorders which respond to α7-nAChR modulation, e.g. psychiatric (e.g. schizophrenia) and/or neurodegenerative disorders (e.g. Alzheimers Disease). WO2004/022556A1 discloses (R)-3-(6-(4-methylphenyl)-pyridin-3-yloxy)-1-aza-bicyclo[2.2.2]octane in free form crystallized from acetonitrile, but does not disclose any specific salts of said compound. (R)-3-(6-(4-methylphenyl)-pyridin-3-yloxy)-1-aza-bicyclo[2.2.2]octane in free form is hygroscopic, has a low aqueous solubility and a low melting point.

Selection criteria for solid forms depend on the planned indications and route(s) of administration. For a CNS-indication, such as schizophrenia, with an envisaged oral route of administration it is important to e.g. achieve a good absorption/oral bioavailability. Typically, suitable solid forms are crystalline forms having a low hygroscopy, a high aqueous solubility, a high melting point and do not exist in multiple forms (e.g. polymorphs, solvates and/or hydrates). Further relevant parameters are safety aspects (e.g. low toxicity), stability in bulk, compatibility with excipients, pH of aqueous solution, good morphology and easy handling.

The invention therefore provides a salt of (R)-3-(6-(4-methylphenyl)-pyridin-3-yloxy)-1-aza-bicyclo[2.2.2]octane wherein said salt is the fumarate, maleate, chloride, phosphate, succinate or malonate salt of (R)-3-(6-(4-methylphenyl)-pyridin-3-yloxy)-1-aza-bicyclo[2.2.2]octane. Unless specified otherwise, said salt will be referred to hereinafter as "SALT OF THE INVENTION".

As used herein "salt" may include hydrates and solvates.

As used herein "crystalline form" refers to a solid form of a molecule, atom and/or ion, in which its constituent atoms, molecules and/or ions are arranged in an orderly repeating pattern extending in all three spatial dimensions.

As used herein "polymorph" refers to crystalline forms having the same chemical composition but different spatial arrangements of the molecules, atoms and/or ions forming the crystal.

As used herein "amorphous form" refers to a solid form of a molecule, atom and/or ion that is not crystalline. An amorphous solid does not display a definitive X-ray diffraction pattern.

As used herein "solvate" refers to a form, e.g. a crystalline form, of a molecule, atom and/or ions that further comprises molecules of a solvent or solvents incorporated into the solid structure, e.g. crystalline lattice structure. The solvent molecules in the solvate may be present in a regular arrangement and/or a non-ordered arrangement. The solvate may comprise either a stoichiometic or nonstoichiometric amount of the solvent molecules. For example, a solvate with a nonstoichiometric amount of solvent molecules may result from partial loss of solvent form the solvate. Solvates may occur as dimers or oligomers comprising more than one molecule of (R)-3-(6-(4-methylphenyl)-pyridin-3-yloxy)-1-aza-bicyclo[2.2.2]octane within a crystalline lattice structure.

As used herein "substantially pure", when used in reference to a solid form, means a compound, e.g. a salt (such as the mono-fumarate of (R)-3-(6-(4-methylphenyl)-pyridin-3-yloxy)-1-aza-bicyclo[2.2.2]octane), having a purity greater than 90 weight %, including greater than 90, 91, 92, 93, 94, 95, 96, 97, 98, and 99 weight %, and also including equal to about 100 weight % of the compound, e.g. of the mono-fumarate of (R)-3-(6-(4-methylphenyl)-pyridin-3-yloxy)-1-aza-bicyclo[2.2.2]octane, based on the weight of the solid form. The remaining material in the solid form may comprise e.g. reaction impurities and/or processing impurities arising from its preparation and/or—if applicable—other form(s) of the compound. For example, a crystalline form of the mono-fumarate of (R)-3-(6-(4-methylphenyl)-pyridin-3-yloxy)-1-aza-bicyclo[2.2.2]octane may be deemed substantially pure in that it has a purity greater than 90 weight %, as measured by means that are at this time known and generally accepted in the art, where the remaining less than 10 weight % of material comprises reaction impurities and/or processing impurities.

As used herein "mono-" in connection with salts, e.g. mono-fumarate salts, refers to a base to acid ratio of about 1:1.

Salts

1. Fumarate Salt:

In embodiment 1, the SALT OF THE INVENTION is the fumarate salt of (R)-3-(6-(4-methylphenyl)-pyridin-3-yloxy)-1-aza-bicyclo[2.2.2]octane, e.g. the mono-fumarate salt of (R)-3-(6-(4-methylphenyl)-pyridin-3-yloxy)-1-aza-bicyclo[2.2.2]octane in crystalline form. The mono-fumarate salt of (R)-3-(6-(4-methylphenyl)-pyridin-3-yloxy)-1-aza-bicyclo[2.2.2]octane in crystalline form may be produced from isopropyl alcohol when one equivalent fumaric acid is used.

The molecular formula is $C_{23}H_{26}N_2O_5$.

It shows good solubility in aqueous media (>30 mg/ml in water, 0.1N Hcl, and pH 6.8 buffer). It is slightly hygroscopic: Loss on drying (LOD) of a sample was <0.03% and moisture gain was 0.5% at 85% relative humidity (RH).

Its melting point was determined by heating at 2° C./minute to be 164-168.5° C. (onset) with subsequent decomposition.

It shows good stability in many buffer solutions and at various pH values. Also the solid-state stability is good.

The X-ray powder diffraction (XRPD) pattern of a sample prepared according to this method (see also Example 1) is shown in FIG. 1. Measurements were performed at a temperature of about 22° C. and an x-ray wavelength, λ, of 1.5418 Å (CuKα λ=1.5418 Å).
Summary of XRPD Pattern:

| No. | 2 theta (deg°) | Intensity |
|---|---|---|
| 1 | 17.4 | 75.2 |
| 2 | 15.2 | 49.8 |
| 3 | 3.8 | 46.3 |
| 4 | 20.1 | 45.2 |
| 5 | 19.8 | 35.7 |
| 6 | 13.7 | 33.8 |
| 7 | 22.8 | 31.2 |
| 8 | 19.2 | 25.9 |
| 9 | 26.7 | 24 |
| 10 | 18.5 | 22.5 |
| 11 | 25.9 | 22.2 |
| 12 | 11.3 | 21.5 |
| 13 | 29.3 | 18.5 |
| 14 | 20.9 | 16.7 |
| 15 | 26.5 | 15.8 |
| 16 | 21.8 | 15.7 |
| 17 | 30.8 | 9.1 |
| 18 | 27.5 | 8.4 |
| 19 | 7.6 | 8.3 |
| 20 | 25.1 | 8 |
| 21 | 23.2 | 7.6 |
| 22 | 36.4 | 7.6 |
| 23 | 23.9 | 7.4 |
| 24 | 38.9 | 6.5 |

In one embodiment, the mono-fumarate salt of (R)-3-(6-(4-methylphenyl)-pyridin-3-yloxy)-1-aza-bicyclo[2.2.2]octane in crystalline form is characterized by an XRPD pattern with at least four, more preferably five, most preferably all of the following peaks at an angle of refraction 2 theta (2θ) of 3.8, 13.7, 15.2, 17.4, 19.8 and 20.1, ±0.2, respectively.

In one embodiment, the mono-fumarate salt of (R)-3-(6-(4-methylphenyl)-pyridin-3-yloxy)-1-aza-bicyclo[2.2.2]octane in crystalline form is characterized by an XRPD pattern substantially the same as the XRPD pattern shown in FIG. 1.

The term "substantially the same" with reference to X-ray diffraction peak positions means that typical peak position and intensity variability are taken into account. For example, one skilled in the art will appreciate that the peak positions (2Θ) will show some inter-apparatus variability, typically as much as 0.2°. Further, one skilled in the art will appreciate that peak intensities will show inter-apparatus variability as well as variability due to degree of crystallinity, preferred orientation, prepared sample surface, and other factors known to those skilled in the art, and should be taken as qualitative measure only.

2. Maleate Salt:

In embodiment 2, the SALT OF THE INVENTION is the maleate salt of (R)-3-(6-(4-methylphenyl)-pyridin-3-yloxy)-1-aza-bicyclo[2.2.2]octane, e.g. the mono-maleate salt of (R)-3-(6-(4-methylphenyl)-pyridin-3-yloxy)-1-aza-bicyclo[2.2.2]octane in crystalline form.

The mono-maleate salt of (R)-3-(6-(4-methylphenyl)-pyridin-3-yloxy)-1-aza-bicyclo[2.2.2]octane in crystalline form may be produced from acetonitrile when one equivalent maleic acid is used.

It shows good solubility in aqueous media (>30 mg/ml in water, 0.1N HCl, and pH 6.8 buffer). It is slightly hygroscopic: LOD of a sample was <0.03% and moisture gain was 0.3% at 85% RH.

Its melting point was determined by heating at 2° C./minute to be 152-154° C. (onset) with subsequent decomposition.

It shows good stability in many buffer solutions and at various pH values. Also the solid-state stability is good.

The XRPD pattern of a sample prepared according to this method (see also Example 2) is shown in FIG. 2. Measurements were performed at a temperature of about 22° C. and an x-ray wavelength, λ, of 1.5418 Å (CuKα λ=1.5418 Å).
Summary of XRPD Pattern:

| No. | 2 theta (deg°) | Intensity |
|---|---|---|
| 1 | 19.1 | 199.1 |
| 2 | 23.5 | 95.4 |
| 3 | 18 | 80.1 |
| 4 | 16 | 54.2 |
| 5 | 12.9 | 46.3 |
| 6 | 19.9 | 45.4 |
| 7 | 12.6 | 45 |
| 8 | 16.5 | 34.1 |
| 9 | 30.5 | 32.1 |
| 10 | 28.7 | 26 |
| 11 | 24.9 | 25.6 |
| 12 | 31.3 | 25.4 |
| 13 | 9.5 | 25.1 |
| 14 | 25.5 | 23.3 |
| 15 | 27.9 | 21.7 |
| 16 | 24.6 | 21.6 |
| 17 | 18.6 | 17.8 |
| 18 | 35 | 17.6 |
| 19 | 21.9 | 15.9 |
| 20 | 26 | 15.9 |
| 21 | 26.4 | 15.6 |
| 22 | 15.6 | 15.2 |
| 23 | 29.8 | 14.4 |
| 24 | 35.8 | 12 |
| 25 | 33.2 | 11.7 |
| 26 | 29.6 | 11.5 |

In one embodiment, the mono-maleate salt of (R)-3-(6-(4-methylphenyl)-pyridin-3-yloxy)-1-aza-bicyclo[2.2.2]octane in crystalline form is characterized by an XRPD pattern with at least four, more preferably five, most preferably all of the following peaks at an angle of refraction 2 theta (2θ) of 12.9, 16.0, 18.0, 19.1, 19.9 and 23.5, ±0.2, respectively.

In one embodiment, the mono-maleate salt of (R)-3-(6-(4-methylphenyl)-pyridin-3-yloxy)-1-aza-bicyclo[2.2.2]octane in crystalline form is characterized by an XRPD pattern substantially the same as the XRPD pattern shown in FIG. 2.

3. Hydrochloride Salt:

In embodiment 3, the SALT OF THE INVENTION is the hydrochloride salt of (R)-3-(6-(4-methylphenyl)-pyridin-3-yloxy)-1-aza-bicyclo[2.2.2]octane, e.g. the mono-hydrochloride salt of (R)-3-(6-(4-methylphenyl)-pyridin-3-yloxy)-1-aza-bicyclo[2.2.2]octane in crystalline form. The mono-hydrochloride salt of (R)-3-(6-(4-methylphenyl)-pyridin-3-yloxy)-1-aza-bicyclo[2.2.2]octane in crystalline form may be produced directly from a synthesis mixture by adding hydrochloric acid.

It shows good solubility in aqueous media (>30 mg/ml).

It is hygroscopic and may form mono- and/or di-hydrates depending on humidity level; when tested, LOD of a sample was about 5% and this amount of water was retained under normal conditions (i.e. at about 40-50% RH). Theoretically, an amount of 5.2% water correlates to 1 water molecule per salt molecule. Moisture gain was about 5% at 85% RH—which would correlate with 2 water molecules per salt molecule.

Its melting point was determined by heating at 2° C./minute to be 240° C. (onset) with subsequent decomposition.

The XRPD pattern of a sample prepared directly from a synthesis mixture (e.g. see Example 3.1.) is shown in FIG. 3. Measurements were performed at a temperature of about 22° C. and an x-ray wavelength, λ, of 1.5418 Å (CuKα λ=1.5418 Å).

Summary of XRPD Pattern:

| No. | 2 theta (deg°) | Intensity |
|---|---|---|
| 1 | 20.8 | 125.1 |
| 2 | 7.3 | 81.4 |
| 3 | 17.2 | 50.9 |
| 4 | 11.6 | 46.6 |
| 5 | 18.4 | 46.3 |
| 6 | 31.1 | 34.8 |
| 7 | 26.7 | 34.3 |
| 8 | 19.7 | 22.7 |
| 9 | 14.6 | 20.7 |
| 10 | 23.5 | 19.9 |
| 11 | 16.3 | 16.6 |
| 12 | 28.8 | 12 |
| 13 | 27.2 | 11.4 |
| 14 | 25 | 10.9 |
| 15 | 22.9 | 10.9 |
| 16 | 13.5 | 8.9 |

In one embodiment, the mono-hydrochloride salt of (R)-3-(6-(4-methylphenyl)-pyridin-3-yloxy)-1-aza-bicyclo[2.2.2]octane in crystalline form is characterized by an XRPD pattern with at least four, more preferably five, most preferably all of the following peaks at an angle of refraction 2 theta (2θ) of 7.3, 11.6, 17.2, 18.4, 20.8 and 31.1, ±0.2, respectively.

In one embodiment, the mono-hydrochloride salt of (R)-3-(6-(4-methylphenyl)-pyridin-3-yloxy)-1-aza-bicyclo[2.2.2]octane in crystalline form is characterized by an XRPD pattern substantially the same as the XRPD pattern shown in FIG. 3.

4. Phosphate Salt:

In embodiment 4, the SALT OF THE INVENTION is the phosphate salt of (R)-3-(6-(4-methylphenyl)-pyridin-3-yloxy)-1-aza-bicyclo[2.2.2]octane, e.g. the mono-phosphate salt of (R)-3-(6-(4-methylphenyl)-pyridin-3-yloxy)-1-aza-bicyclo[2.2.2]octane in crystalline form.

It was discovered, that said phosphate salt exists in more than one solid form.

4.1. Form A of the Mono-Phosphate Salt:

A mono-phosphate salt of (R)-3-(6-(4-methylphenyl)-pyridin-3-yloxy)-1-aza-bicyclo[2.2.2]octane in crystalline form may be produced from ethanol when one equivalent phosphoric acid is used.

The XRPD pattern of a sample prepared according to this method (see also Example 4.1) is shown in FIG. 4A. Measurements were performed at a temperature of about 22° C. and an x-ray wavelength, λ, of 1.5418 Å (CuKα λ=1.5418 Å).

Summary of XRPD Pattern:

| No. | 2 theta (deg°) | Intensity |
|---|---|---|
| 1 | 17.7 | 76.3 |
| 2 | 14.3 | 76 |
| 3 | 18.2 | 75.1 |
| 4 | 19.7 | 64.9 |
| 5 | 16.5 | 56.3 |
| 6 | 4.7 | 46.6 |
| 7 | 20 | 40.2 |
| 8 | 21.8 | 29.7 |
| 9 | 26 | 24.4 |
| 10 | 18.8 | 20.7 |
| 11 | 12.2 | 16.3 |
| 12 | 30.4 | 13.8 |
| 13 | 25.7 | 13.2 |
| 14 | 22.8 | 12.8 |
| 15 | 22.5 | 12.6 |
| 16 | 29.4 | 12.5 |
| 17 | 35 | 10.6 |

In one embodiment, the mono-phosphate salt of (R)-3-(6-(4-methylphenyl)-pyridin-3-yloxy)-1-aza-bicyclo[2.2.2]octane in crystalline form is characterized by an XRPD pattern with at least four, more preferably five, most preferably all of the following peaks at an angle of refraction 2 theta (2θ) of 4.7, 14.3, 16.5, 17.7, 18.2 and 19.7, ±0.2, respectively.

In one embodiment, the mono-phosphate salt of (R)-3-(6-(4-methylphenyl)-pyridin-3-yloxy)-1-aza-bicyclo[2.2.2]octane in crystalline form is characterized by an XRPD pattern substantially the same as the XRPD pattern shown in FIG. 4A.

Form A of the mono-phosphate salt shows good solubility in aqueous media (>30 mg/ml). It is slightly hygroscopic: when tested, LOD of a sample was about 0.5% and moisture gain was 0.2% at 85% RH.

Its melting/decomposition point was determined by heating at 2° C./minute to be about 222° C.

4.2. Form B of the Phosphate Salt:

Another form of the phosphate salt of (R)-3-(6-(4-methylphenyl)-pyridin-3-yloxy)-1-aza-bicyclo[2.2.2]octane in crystalline form (Form B of the phosphate salt) was found as described in the Examples section (see Example 4.2). The associated XRPD pattern is shown in FIG. 4B.

Summary of XRPD Pattern:

| No. | 2 theta (deg°) | Intensity |
|---|---|---|
| 1 | 14.5 | 131.9 |
| 2 | 14 | 106.9 |
| 3 | 14.2 | 101.1 |
| 4 | 15.6 | 62.4 |
| 5 | 19.7 | 51.5 |
| 6 | 19.3 | 42.3 |
| 7 | 13.1 | 36 |
| 8 | 16.8 | 34.2 |
| 9 | 20 | 32.6 |
| 10 | 18 | 30.4 |
| 11 | 12.4 | 29.2 |
| 12 | 22.6 | 24.4 |
| 13 | 16.4 | 20.7 |
| 14 | 4.2 | 19.3 |
| 15 | 10.4 | 18 |
| 16 | 23 | 17.8 |
| 17 | 11.5 | 17.4 |
| 18 | 15.1 | 15.6 |
| 19 | 32.6 | 14.2 |
| 20 | 12 | 13.7 |
| 21 | 20.7 | 13.6 |
| 22 | 24.7 | 12.9 |
| 23 | 21 | 12.7 |
| 24 | 23.5 | 12.5 |
| 25 | 25.8 | 11.2 |
| 26 | 9 | 11.1 |
| 27 | 9.6 | 10.8 |
| 28 | 30.5 | 9.6 |
| 29 | 25.2 | 9.4 |
| 30 | 33.8 | 9.3 |
| 31 | 27.1 | 9.1 |
| 32 | 33.3 | 8.8 |

| No. | 2 theta (deg°) | Intensity |
|---|---|---|
| 33 | 30.1 | 8 |
| 34 | 7.8 | 8 |
| 35 | 31.5 | 7.5 |
| 36 | 8.3 | 7.2 |
| 37 | 29.6 | 7.2 |
| 38 | 26.7 | 6.8 |
| 39 | 29.1 | 6.4 |
| 40 | 7.1 | 6.2 |

4.3. Form C of the Phosphate Salt:

Another form of the phosphate salt of (R)-3-(6-(4-methylphenyl)-pyridin-3-yloxy)-1-aza-bicyclo[2.2.2]octane in crystalline form (Form C of the phosphate salt) was found as described in the Examples section (see Example 4.3). The associated XRPD pattern is shown in FIG. 4C.

Summary of XRPD Pattern:

| No. | 2 theta (deg°) | Intensity |
|---|---|---|
| 1 | 4.6 | 155.5 |
| 2 | 14.9 | 68.8 |
| 3 | 16.9 | 54.8 |
| 4 | 17.7 | 50.4 |
| 5 | 19.9 | 47.6 |
| 6 | 18.6 | 44.6 |
| 7 | 13.9 | 44.5 |
| 8 | 21.6 | 37.5 |
| 9 | 20.2 | 36.2 |
| 10 | 25.8 | 32.8 |
| 11 | 18 | 22.9 |
| 12 | 30.1 | 17.4 |
| 13 | 22.7 | 16.2 |
| 14 | 29.4 | 16 |
| 15 | 12.1 | 11.1 |
| 16 | 7.2 | 9.7 |

5. Succinate Salt:

In embodiment 5, the SALT OF THE INVENTION is the succinate salt of (R)-3-(6-(4-methylphenyl)-pyridin-3-yloxy)-1-aza-bicyclo[2.2.2]octane, e.g. the mono-succinate salt of (R)-3-(6-(4-methylphenyl)-pyridin-3-yloxy)-1-aza-bicyclo[2.2.2]octane in crystalline form.

It was discovered, that said mono-succinate salt exists in more than one solid form.

5.1 Form A of the Mono-Succinate Salt

A mono-succinate salt of (R)-3-(6-(4-methylphenyl)-pyridin-3-yloxy)-1-aza-bicyclo[2.2.2]octane in crystalline form may be produced from ethanol when one equivalent succinic acid is used.

The XRPD pattern of a sample prepared according to this method (see also Example 5) is shown in FIG. 5A. Measurements were performed at a temperature of about 22° C. and an x-ray wavelength, λ, of 1.5418 Å (CuKα λ=1.5418 Å).

Summary of XRPD Pattern:

| No. | 2 theta (deg°) | Intensity |
|---|---|---|
| 1 | 17.4 | 178.5 |
| 2 | 19.4 | 161.1 |
| 3 | 10.7 | 45.4 |
| 4 | 15.2 | 38.7 |
| 5 | 15.8 | 31.5 |
| 6 | 23.7 | 28.2 |
| 7 | 13.3 | 28.1 |
| 8 | 21.8 | 24.8 |
| 9 | 18.4 | 23.7 |
| 10 | 12.9 | 19.5 |
| 11 | 14.8 | 17.1 |
| 12 | 9.2 | 15.2 |
| 13 | 29.1 | 15 |
| 14 | 23 | 14.6 |
| 15 | 6.5 | 14.6 |
| 16 | 25.3 | 13.1 |
| 17 | 30 | 12.5 |
| 18 | 24.6 | 11.4 |
| 19 | 32.9 | 11 |

In one embodiment, the mono-succinate salt of (R)-3-(6-(4-methylphenyl)-pyridin-3-yloxy)-1-aza-bicyclo[2.2.2]octane in crystalline form is characterized by an XRPD pattern with at least four, more preferably five, most preferably all of the following peaks at an angle of refraction 2 theta (2θ) of 10.7, 15.2, 15.8, 17.4, 19.4 and 23.7, ±0.2, respectively.

In one embodiment, the mono-succinate salt of (R)-3-(6-(4-methylphenyl)-pyridin-3-yloxy)-1-aza-bicyclo[2.2.2]octane in crystalline form is characterized by an XRPD pattern substantially the same as the XRPD pattern shown in FIG. 5A.

Form A of the mono-succinate salt shows good solubility in aqueous media (2-15 mg/ml). It is considered to be a monohydrate: when tested, LOD of a sample was about 4.5%. Theoretically, an amount of 4.1% water correlates to 1 water molecule per salt molecule. Moisture gain was 0.3% at 85% RH.

Its melting point was determined by heating at 2° C./minute to be 113° C. (onset) with subsequent decomposition.

5.2. Form B of the Mono-Succinate Salt:

Another form of the succinate salt of (R)-3-(6-(4-methylphenyl)-pyridin-3-yloxy)-1-aza-bicyclo[2.2.2]octane in crystalline form (Form B of the mono-succinate salt) was found as described in the Examples section (see Example 5.2). The associated XRPD pattern is shown in FIG. 5B.

Summary of XRPD Pattern:

| No. | 2 theta (deg°) | Intensity |
|---|---|---|
| 1 | 7.7 | 2279 |
| 2 | 18.1 | 1417 |
| 3 | 3.8 | 909 |
| 4 | 20.8 | 901 |
| 5 | 17 | 816 |
| 6 | 22.3 | 765 |
| 7 | 15.5 | 639 |
| 8 | 23.9 | 578 |
| 9 | 24 | 564 |
| 10 | 19.4 | 463 |
| 11 | 16.9 | 462 |
| 12 | 25.5 | 423 |
| 13 | 18.8 | 418 |
| 14 | 21.9 | 367 |
| 15 | 22.7 | 306 |
| 16 | 27.4 | 301 |
| 17 | 24.5 | 292 |
| 18 | 13.8 | 273 |
| 19 | 11.6 | 226 |

6. Malonate Salt:

In embodiment 6, the SALT OF THE INVENTION is the malonate salt of (R)-3-(6-(4-methylphenyl)-pyridin-3- yloxy)-1-aza-bicyclo[2.2.2]octane, e.g. the mono-malonate salt of (R)-3-(6-(4-methylphenyl)-pyridin-3-yloxy)-1-aza-bicyclo[2.2.2]octane in crystalline form. The mono-malonate salt of (R)-3-(6-(4-methylphenyl)-pyridin-3-yloxy)-1-aza-bicyclo[2.2.2]octane in crystalline form may be produced from acetonitrile when one equivalent malonic acid is used.

It shows good solubility in aqueous media (>30 mg/ml).

It is slightly hygroscopic: when tested, LOD of a sample was 0% and moisture gain was 1.3% at 85% RH.

Its melting point was determined by heating at 2° C./minute to be 140° C. (onset) with subsequent decomposition.

The XRPD pattern of a sample prepared according to this method (see also Example 6) is shown in FIG. 6. Measurements were performed at a temperature of about 22° C. and an x-ray wavelength, $\lambda$, of 1.5418 Å (CuK$\alpha$ $\lambda$=1.5418 Å).

Summary of XRPD Pattern:

| No. | 2 theta (deg°) | Intensity |
|---|---|---|
| 1 | 5 | 78.1 |
| 2 | 24.3 | 75 |
| 3 | 16.8 | 63.2 |
| 4 | 18.1 | 55.8 |
| 5 | 13 | 53.2 |
| 6 | 19.8 | 53 |
| 7 | 17.1 | 52.3 |
| 8 | 15.6 | 51.9 |
| 9 | 20.2 | 50.7 |
| 10 | 18.7 | 33 |
| 11 | 15.1 | 31.3 |
| 12 | 29.1 | 28.5 |
| 13 | 12.2 | 23.6 |
| 14 | 28.8 | 23.5 |
| 15 | 27.5 | 21.4 |
| 16 | 27 | 20.1 |
| 17 | 20.9 | 18 |
| 18 | 30.1 | 17.9 |
| 19 | 32.2 | 14.3 |
| 20 | 31 | 13.4 |
| 21 | 14.3 | 13.3 |
| 22 | 10.2 | 11.8 |
| 23 | 21.4 | 11.3 |
| 24 | 34 | 10.6 |
| 25 | 33.5 | 10.5 |
| 26 | 25.9 | 9.4 |
| 27 | 25.2 | 9.1 |
| 28 | 34.5 | 8.7 |
| 29 | 35.8 | 8.3 |
| 30 | 35.2 | 7.2 |

In one embodiment, the mono-malonate salt of (R)-3-(6-(4-methylphenyl)-pyridin-3-yloxy)-1-aza-bicyclo[2.2.2]octane in crystalline form is characterized by an XRPD pattern with at least four, more preferably five, most preferably all of the following peaks at an angle of refraction 2 theta (2$\theta$) of 5.0, 13.0, 16.8, 18.1, 19.8 and 24.3, ±0.2, respectively.

In one embodiment, the mono-malonate salt of (R)-3-(6-(4-methylphenyl)-pyridin-3-yloxy)-1-aza-bicyclo[2.2.2]octane in crystalline form is characterized by an XRPD pattern substantially the same as the XRPD pattern shown in FIG. 6.

Preparation Methods for Crystalline Forms

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, 2$^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization (see "Programmed Cooling of Batch Crystallizers," J. W. Mullin and J. Nyvlt, *Chemical Engineering Science*, 1971, 26, 369-377). In general, seed crystals of small size are used. Seed crystals of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be delumped by sieving or forced sieving, if necessary.

Crystalline forms may be prepared directly from the reaction medium of the final process for preparing (R)-3-(6-(4-methylphenyl)-pyridin-3-yloxy)-1-aza-bicyclo[2.2.2]octane or a SALT OF THE INVENTION. This may be achieved, for example, by employing in the final process step a solvent or a mixture of solvents from which the SALT OF THE INVENTION may be crystallized. Alternatively, crystalline forms may be obtained by distillation or solvent addition techniques. Suitable solvents for this purpose include, for example, nonpolar solvents and polar solvents, including protic polar solvents such as alcohols, and aprotic polar solvents such as ketones.

The presence of more than one polymorph in a sample may be determined by techniques such as powder x-ray diffraction (PXRD) or solid state nuclear magnetic resonance spectroscopy. For example, the presence of extra peaks in the comparison of an experimentally measured PXRD pattern with a simulated PXRD pattern may indicate more than one polymorph in the sample. The simulated PXRD may be calculated from single crystal x-ray data; see Smith, D. K., "*A FORTRAN Program for Calculating X-Ray Powder Diffraction Patterns*," Lawrence Radiation Laboratory, Livermore, Calif., UCRL-7196 (April 1963).

In many cooled and/or seeded crystallizations of the monofumarate salt of (R)-3-(6-(4-methylphenyl)-pyridin-3-yloxy)-1-aza-bicyclo[2.2.2]octane fine particles are obtained. Fine particles typically have the drawback of bad filtration properties and poor flowability, which is especially disadvantageous for the widely used dry-granulation using roller compaction. It was found that, depending on crystallization techniques, a mean particle size of the crystals of above 15 µm can be obtained. As laid out above, such mean particle sizes are especially suitable for formulation work.

The term "mean particle size" ($X_{50}$) refers to a crystal size distribution wherein 50% of crystals related to the total volume of particles have a smaller diameter of an equivalent sphere than the value given.

The term "$X_{90}$" refers to a crystal size distribution wherein 90% of crystals related to the total volume of particles have a smaller diameter of an equivalent sphere than the value given.

The term "$X_{10}$" refers to a crystal size distribution wherein 10% of crystals related to the total volume of particles have a smaller diameter of an equivalent sphere than the value given.

Consequently, one embodiment of the invention is a method of preparing a mono-fumarate salt of (R)-3-(6-(4-methylphenyl)-pyridin-3-yloxy)-1-aza-bicyclo[2.2.2]octane in crystalline form comprising the steps of
(a) preparing a solution of a mono-fumarate salt of (R)-3-(6-(4-methylphenyl)-pyridin-3-yloxy)-1-aza-bicyclo[2.2.2]octane in a solvent mixture of a primary alcohol, a secondary alcohol and water, wherein the primary alcohol:secondary alcohol volume ratio is from 9:1 to 1:1, and wherein the alcohols:water volume ratio is from 9:1 to 19:1;
(b) heating the solution of step (a) to elevated temperature;
(c) adding the solution of step (b) gradually to an ether antisolvent at a temperature ranging from ambient temperature to 55° C. until a solution from step (b): ether antisolvent volume ratio from 1:1 to 1:5 is reached; wherein after an amount of the solution of step (b) from 10% to 40% of the total amount is added, the resulting solution is seeded with seed crystals of a mono-fumarate salt of (R)-3-(6-(4-methylphenyl)-pyridin-3-yloxy)-1-aza-bicyclo[2.2.2]octane in crystalline form, wherein the seed crystals are suspended in a secondary alcohol;
(d) cooling the seeded solution of step (c) gradually to a temperature below ambient; and
(e) isolate the solids by filtration to obtain the mono-fumarate salt of (R)-3-(6-(4-methylphenyl)-pyridin-3-yloxy)-1-aza-bicyclo[2.2.2]octane in crystalline form.

Examples of primary alcohols are methanol or ethanol. An example of a secondary alcohol is isopropanol. An example of an ether antisolvent is tertiary-butylmethylether.

Typically, the mean particle size of the seed crystals is from 1 µm to 10 µm. Typically the seed crystals are added in an amount of from 0.08% to 2% of the amount of the salt in step (a).

One embodiment of the invention is a method of preparing a mono-fumarate salt of (R)-3-(6-(4-methylphenyl)-pyridin-3-yloxy)-1-aza-bicyclo[2.2.2]octane in crystalline form comprising the steps of
(a) preparing a solution of a mono-fumarate salt of (R)-3-(6-(4-methylphenyl)-pyridin-3-yloxy)-1-aza-bicyclo[2.2.2]octane in a mixture of ethanol, isopropanol and water, wherein the ethanol:isopropanol volume ratio is about 75:15, and wherein the alcohols:water volume ratio is about 90:10;
(b) heating the solution of step (a) to a temperature of about 50° C.;
(c) adding the solution of step (b) gradually to tertiary-butylmethylether at a temperature of about 50° C. until a a solution from step (b): tertiary-butylmethylether volume ratio of about 75:25 is reached; wherein after an amount of the solution of step (b) of about 25% of the total amount is added, the resulting solution is seeded with seed crystals of a mono-fumarate salt of (R)-3-(6-(4-methylphenyl)-pyridin-3-yloxy)-1-aza-bicyclo[2.2.2]octane in crystalline form, wherein the mean particle size of the seed crystals is about 10 µm, wherein the seed crystals are added in an amount of about 0.08% of the amount of the salt in step (a), and wherein the seed crystals are suspended in isopropanol;
(d) cooling the seeded solution of step (c) gradually to a temperature ranging of about 0° C.; and
(e) isolate the solids by filtration to obtain the mono-fumarate salt of (R)-3-(6-(4-methylphenyl)-pyridin-3-yloxy)-1-aza-bicyclo[2.2.2]octane in crystalline form.

One further embodiment of the invention is mono-fumarate salt of (R)-3-(6-(4-methylphenyl)-pyridin-3-yloxy)-1-aza-bicyclo[2.2.2]octane in crystalline form, wherein the mean particle size of the crystals is at least 15 µm.

One further embodiment of the invention is mono-fumarate salt of (R)-3-(6-(4-methylphenyl)-pyridin-3-yloxy)-1-aza-bicyclo[2.2.2]octane in crystalline form, wherein the mean particle size of the crystals is at least 20 µm.

One further embodiment of the invention is mono-fumarate salt of (R)-3-(6-(4-methylphenyl)-pyridin-3-yloxy)-1-aza-bicyclo[2.2.2]octane in crystalline form, wherein the mean particle size of the crystals is at least 25 µm.

One further embodiment of the invention is mono-fumarate salt of (R)-3-(6-(4-methylphenyl)-pyridin-3-yloxy)-1-aza-bicyclo[2.2.2]octane in crystalline form, wherein the mean particle size of the crystals is from 20 µm to 35 µm.

One further embodiment of the invention is mono-fumarate salt of (R)-3-(6-(4-methylphenyl)-pyridin-3-yloxy)-1-aza-bicyclo[2.2.2]octane in crystalline form, wherein the mean particle size of the crystals is from 20 µm to 35 µm; the $X_{10}$ is from 3 µm to 10 µm; and the $X_{90}$ is from 70 µm to 90 µm.

One further embodiment of the invention is mono-fumarate salt of (R)-3-(6-(4-methylphenyl)-pyridin-3-yloxy)-1-aza-bicyclo[2.2.2]octane in crystalline form, wherein the mean particle size of the crystals is from 25 µm to 30 µm.

Analysis of Solid Forms

The solid form of a SALT OF THE INVENTION may be characterized using various techniques, the operation of which are well known to those of ordinary skill in the art.

The forms may be characterized and distinguished using single crystal x-ray diffraction, which is based on unit cell measurements of a single crystal of the form at a fixed analytical temperature. A detailed description of unit cells is provided in Stout & Jensen, X-Ray Structure Determination: A Practical Guide, Macmillan Co., New York (1968), Chapter 3. Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, both run at the same analytical temperature, and measurements for the subject form characterized as a series of 2θ values (usually four or more).

Other means of characterizing the form may be used, such as solid state nuclear magnetic resonance (NMR), differential scanning calorimetry, thermography and gross examination of the crystalline or amorphous morphology. These parameters may also be used in combination to characterize the subject form.

Mean particle sizes, $X_{90}$ and $X_{10}$ are typically measured by Fraunhofer light diffraction.

Utility

SALTS OF THE INVENTION exhibit valuable pharmacological properties administered to animals/humans, and are therefore useful as pharmaceuticals. SALTS OF THE INVENTION are selective α7-nAChR partial agonists.

Due to their pharmacological profiles, SALTS OF THE INVENTION are anticipated to be useful for the treatment of diseases or conditions as diverse as CNS related diseases, PNS related diseases, diseases related to inflammation, pain and withdrawal symptoms caused by an abuse of chemical substances.

Diseases or disorders related to the CNS include general anxiety disorders, cognitive disorders, learning and memory deficits and dysfunctions, Alzheimer's disease (AD), prodromal AD, mild cognitive impairment in the elderly (MCI), amnestic MCI, age associated memory impairment, attention deficit and hyperactivity disorder (ADHD), Parkinson's disease, L-dopa induced dyskinesias associated with Parkinson's disease, Huntington's disease, ALS, prionic neurodegenerative disorders such as Creutzfeld-Jacob disease and kuru disease, Gilles de la Tourette's syndrome, psychosis, depression and depressive disorders, mania, manic depression, schizophrenia, the cognitive deficits in schizophrenia, obsessive compulsive disorders, panic disorders, eating disorders, nociception, AIDS-dementia, senile dementia, mild cognitive dysfunctions related to age, autism, dyslexia, tardive dyskinesia, epilepsy, and convulsive disorders, post-traumatic stress disorders, transient anoxia, pseudodementia, pre-menstrual syndrome, late luteal phase syndrome and jet lag.

Furthermore, SALTS OF THE INVENTION may be useful for the treatment of endocrine disorders, such as thyrotoxicosis, pheochromocytoma, hypertension and arrhythmias as well as angina pectoris, hyperkinesia, premature ejaculation and erectile difficulty.

Still further, SALTS OF THE INVENTION may be useful in the treatment of inflammatory disorders (Wang et al., Nature 2003, 421, 384; de Jonge et al., Nature Immunology 2005, 6, 844; Saeed et al., JEM 2005, 7, 1113), disorders or conditions including inflammatory skin disorders, rheumatoid arthritis, post-operative ileus, Crohn's disease, inflammatory bowel disease, ulcerative colitis, sepsis, fibromyalgia, pancreatitis and diarrhoea.

SALTS OF THE INVENTION may further be useful for the treatment of withdrawal symptoms caused by termination of the use of addictive substances, like heroin, cocaine, tobacco, nicotine, opioids, benzodiazepines and alcohol.

Furthermore, SALTS OF THE INVENTION may be useful for the treatment of pain, e.g. caused by migraine, post-operative pain, phantom limb pain or pain associated with cancer. The pain may comprise inflammatory or neuropathic pain, central pain, chronic headache, pain related to diabetic neuropathy, to post therapeutic neuralgia or to peripheral nerve injury.

Furthermore, degenerative ocular disorders which may be treated include ocular diseases which may directly or indirectly involve the degeneration of retinal cells, including ischemic retinopathies in general, anterior ischemic optic neuropathy, all forms of optic neuritis, age-related macular degeneration (AMD), in its dry forms (dry AMD) and wet forms (wet AMD), diabetic retinopathy, cystoid macular edema (CME), retinal detachment, retinitis pigmentosa, Stargardt's disease, Best's vitelliform retinal degeneration, Leber's congenital amaurosis and other hereditary retinal degenerations, pathologic myopia, retinopathy of prematurity, and Leber's hereditary optic neuropathy.

SALTS OF THE INVENTION can be combined with at least one compound selected from the group consisting of (a) conventional antipsychotics and (b) atypical antipsychotics, in which the antipsychotic is present in free form or in the form of a pharmaceutically acceptable salt; for simultaneous, separate or sequential use to treat psychiatric disorders. The term "psychiatric disorders" as used herein includes, but is not limited to schizophrenia, anxiety disorders, depression and bipolar disorders. Preferably, the psychiatric disorder is schizophrenia, more preferably schizophrenia which is refractory to monotherapy employing one of the combination partners alone.

The term "conventional antipsychotics" as used herein includes, but is not limited to haloperidol, fluphenazine, thiotixene and flupentixol.

The term "atypical antipsychotics" as used herein includes, but is not limited to clozaril, risperidone, olanzapine, quetiapine, ziprasidone and aripiprazol.

SALTS OF THE INVENTION are useful in the treatment of the above diseases/conditions.

Consequently, the invention also relates to a SALT OF THE INVENTION (e.g. the mono-fumarate salt of (R)-3-(6-(4-methylphenyl)-pyridin-3-yloxy)-1-aza-bicyclo[2.2.2]octane in crystalline form) for use as a medicament.

In another embodiment, the invention also relates to a SALT OF THE INVENTION (e.g. the mono-fumarate salt of (R)-3-(6-(4-methylphenyl)-pyridin-3-yloxy)-1-aza-bicyclo[2.2.2]octane in crystalline form) for use in the prevention, treatment and/or delay of progression of a disease or condition, in which α7-nAChR activation plays a role or is implicated.

In another embodiment, the invention also relates to a SALT OF THE INVENTION (e.g. the mono-fumarate salt of (R)-3-(6-(4-methylphenyl)-pyridin-3-yloxy)-1-aza-bicyclo[2.2.2]octane in crystalline form) for use in the prevention, treatment and/or delay of progression of a psychiatric or neurodegenerative disorder.

In another embodiment, the invention also relates to the use of a SALT OF THE INVENTION (e.g. the mono-fumarate salt of (R)-3-(6-(4-methylphenyl)-pyridin-3-yloxy)-1-aza-bicyclo[2.2.2]octane in crystalline form) for the manufacture of a medicament for the prevention, treatment and/or delay of progression of a disease or condition, in which α7-nAChR activation plays a role or is implicated.

In another embodiment, the invention also relates to the use of a SALT OF THE INVENTION (e.g. the mono-fumarate salt of (R)-3-(6-(4-methylphenyl)-pyridin-3-yloxy)-1-aza-bicyclo[2.2.2]octane in crystalline form) for the manufacture of a medicament for the prevention, treatment and/or delay of progression of a psychiatric or neurodegenerative disorder.

In another embodiment, the invention also relates to a method for the prevention, treatment and I or delay of progression of a disease or condition, in which α7-nAChR activation plays a role or is implicated, in a subject in need of such treatment, which comprises administering to such subject a therapeutically effective amount of a SALT OF THE INVENTION (e.g. the mono-fumarate salt of (R)-3-(6-(4-methylphenyl)-pyridin-3-yloxy)-1-aza-bicyclo[2.2.2]octane in crystalline form).

In another embodiment, the invention relates to a method for the prevention, treatment and/or delay of progression of a psychiatric or neurodegenerative disorder in a subject in need of such treatment, which comprises administering to such subject a therapeutically effective amount of a SALT OF THE INVENTION (e.g. the mono-fumarate salt of (R)-3-(6-(4-methylphenyl)-pyridin-3-yloxy)-1-aza-bicyclo[2.2.2]octane in crystalline form).

In another embodiment, the invention relates to a method for the prevention, treatment and/or delay of progression of a disease or condition, in which α7-nAChR activation plays a role or is implicated, in a subject in need thereof, which comprises (i) diagnosing said disease or condition in said subject and (ii) administering to said subject a therapeutically effective amount of a SALT OF THE INVENTION (e.g. the mono-fumarate salt of (R)-3-(6-(4-methylphenyl)-pyridin-3-yloxy)-1-aza-bicyclo[2.2.2]octane in crystalline form).

In another embodiment, the invention relates to a method for the prevention, treatment and/or delay of progression of a psychiatric or neurodegenerative disorder, in a subject in need thereof, which comprises (i) diagnosing said disorder in said subject and (ii) administering to said subject a therapeutically effective amount of a SALT OF THE INVENTION (e.g. the mono-fumarate salt of (R)-3-(6-(4-methylphenyl)-pyridin-3-yloxy)-1-aza-bicyclo[2.2.2]octane in crystalline form).

Treatment may comprise a reduction in the characteristics associated with the disease, condition or disorder, including, although not limited to, e.g. for schizophrenia: reduction in positive symptoms, negative symptoms, mood symptoms and/or cognitive symptoms and/or reduction in impulsive or violent behaviour.

In the case of prophylactic treatment, the SALT OF THE INVENTION may be used to delay or prevent the onset of the Instant Movement Disorder.

The term "subject" as used herein refers preferably to a human being, especially to a patient being diagnosed with the disease, condition or disorder.

The term "therapeutically effective amount" as used herein typically refers to a drug amount which, when administered to a subject, is sufficient to provide a therapeutic benefit, e.g. is sufficient for treating, preventing or delaying the progression of the disease, condition or disorder (e.g. the amount provides an amelioration of symptoms, e.g. it leads to a reduction of positive symptoms in schizophrenic patients).

For the above-mentioned indications (the diseases, conditions and/or disorders) the appropriate dosage will vary depending upon, for example, the host, the mode of administration and the nature and severity of the condition being treated. However, in general, satisfactory results in animals are indicated to be obtained at a daily dosage of from about 0.01 to about 100 mg/kg body weight, preferably from about 0.1 to about 10 mg/kg body weight, e.g. 1 mg/kg. In larger mammals, for example humans, an indicated daily dosage is in the range from about 0.1 to about 1000 mg, preferably from about 1 to about 400 mg, most preferably from about 3 to about 100 mg of a SALT OF THE INVENTION conveniently administered, for example, in divided doses up to four times a day.

Amorphous forms/crystalline forms of SALTS OF THE INVENTION are useful as intermediates for preparing crystalline forms/other crystalline forms of SALTS OF THE INVENTION that are useful in the treatment of the above diseases/conditions.

Formulations Comprising Salts of the Invention

SALTS OF THE INVENTION may be used alone or in combination, or formulated with one or more excipients and/or other active pharmaceutical ingredients to provide formulations suitable for the treatment of the above diseases/conditions.

The invention therefore also relates to a pharmaceutical composition comprising a SALT OF THE INVENTION as active ingredient and at least one pharmaceutically acceptable carrier.

A pharmaceutical composition according to the invention is, preferably, suitable for enteral administration, such as oral or rectal administration; or parenteral administration, such as intramuscular, intravenous, nasal or transdermal administration, to a warm-blooded animal (human beings and animals) that comprises a therapeutically effective amount of the active ingredients and one or more suitable pharmaceutically acceptable carriers.

Preferred are compositions for oral or transdermal administration.

A composition for enteral or parenteral administration is, for example, a unit dosage form, such as a coated tablet, a tablet, a capsule, a suppository or an ampoule.

The unit content of active ingredient(s) in an individual dose need not in itself constitute a therapeutically effective amount, since such an amount can be reached by the administration of a plurality of dosage units.

A composition according to the invention may contain from e.g. 0.1 to 100% active ingredient(s) by weight, e.g. from 1 to 10% by weight, e.g. from 11 to 25% by weight, or from 20 to 60% by weight.

If not indicated otherwise, a pharmaceutical composition according to the invention is prepared in a manner known per se, e.g. by means of conventional mixing, granulating, sugar-coating, dissolving or lyophilizing processes. In preparing e.g. a composition for an oral dosage form, any of the usual pharmaceutical carriers may be employed, for example water, glycols, oils, alcohols, fillers, such as starches, sugars, or microcrystalline cellulose, granulating agents, lubricants, binders, disintegrants, gliding agents and the like. Because of their ease of administration, tablets and capsules represent the most advantageous oral dosage unit forms, in which case solid pharmaceutical carriers are obviously employed.

Examples of fillers are a starch, e.g. maize starch or corn starch; a sugar, e.g. sprayed lactose; or a cellulose, e.g. microcrystalline cellulose (e.g. Avicel®), methylcellulose, hydroxypropylcellulose, hydroxypropylmethylcellulose. Fillers typically are present in an amount of from e.g. 1 to 70% by weight.

Examples of disintegrants are sodium starch glycolate, e.g. sodium starch glycolate type A; sodium or calcium carboxymethyl cellulose (sodium or calcium carmellose); crosslinked sodium carboxymethyl cellulose (sodium croscarmellose); starch; hydroxypropyl starch; lactose monohydrate and corn starch; chitosan; povidone; or crosslinked povidone (crospovidone). Disintegrants typically are present in an amount of from e.g. 0.5 to 15% by weight, especially 1.5 to 5% by weight.

Examples of lubricants are stearic acid, magnesium stearate, calcium stearate, zinc stearate, glyceryl palmitostearate, sodium stearyl fumarate, sodium lauryl sulfate, glyceryl behenates, hydrogenated vegetable oils, wax cetyl esters or talc. Lubricants typically are present in an amount of from typically 0.5 to 10% by weight, especially 1.5 to 3% by weight.

Examples of gliding agents are colloidal silicon dioxide, talc, tribasic calcium phosphate, powdered cellulose, hydrophobic colloidal silica, magnesium oxide, magnesium silicate, magnesium trisilicate. Gliding agents typically are present in an amount of from e.g. 0.01 to 5% by weight, especially 0.1 to 1% by weight.

Tablets may optionally be coated, for instance with talc or a polysaccharide (e.g. cellulose) or hydroxypropylmethylcellulose coating. As an example, the coating formulation could be one of the formulations described in the table below or a mixture of them.

|  | Colour | | | |
| --- | --- | --- | --- | --- |
|  | White (w/w)% | Yellow (w/w)% | Red (w/w)% | Black (w/w)% |
| Hydroxypropyl methylcellulose 3 cps | 60-80 | 60-80 | 60-80 | 60-80 |
| Polyethylene glycol 4000 | 5-10 | 5-10 | 5-10 | 5-10 |
| Talc | 5-10 | 5-10 | 5-10 | 5-10 |
| Titanium dioxide | 1-20 | — | — | — |
| Iron oxide yellow | — | 1-20 | — | — |
| Iron oxide red | — | — | 1-20 | — |
| Iron oxide black | — | — | — | 1-20 |

The invention also relates to a pharmaceutical composition comprising mono-fumarate of (R)-3-(6-(4-methylphenyl)-pyridin-3-yloxy)-1-aza-bicyclo[2.2.2]octane as active ingredient and at least one pharmaceutically acceptable carrier, wherein the composition is in the form of a tablet.

The invention also relates to a pharmaceutical composition comprising mono-fumarate of (R)-3-(6-(4-methylphenyl)-pyridin-3-yloxy)-1-aza-bicyclo[2.2.2]octane as active ingredient and at least one pharmaceutically acceptable carrier, wherein the composition is in the form of a capsule.

Tablets/capsules need to be in a certain size range: they should be not too big to avoid discomfort/problems when swallowed; but also not too small as they need to be reliably packaged and they should be easy to handle e.g. during multiple patient dosing in hospitals and/or individual dosing by elderly patients themselves.

It is furthermore important that they have good physico-chemical and storage properties. The tablets/capsules should be easy to manufacture and should show a high level of uniformity in the distribution of the active ingredient throughout the composition.

It is particularly important that the active ingredient remains chemically stable over a potential long shelf time. When assessing storage stability, relative amounts of individual degradation products compared to the total amount of active ingredient are taken into consideration. Individual degradation products should all be present in low relative amounts to ensure that no single product can reach a non-acceptable level, e.g. when the active ingredient is administered in high doses.

It has been found that mono-fumarate of (R)-3-(6-(4-methylphenyl)-pyridin-3-yloxy)-1-aza-bicyclo[2.2.2]octane is very stable in tablets where only certain lubricants are used.

The invention also relates to a pharmaceutical composition in the form of a tablet comprising
(a) mono-fumarate of (R)-3-(6-(4-methylphenyl)-pyridin-3-yloxy)-1-aza-bicyclo[2.2.2]octane as active ingredient;
(b) a filler;
(c) a disintegrant;
(d) a lubricant; and
(e) a gliding agent;
wherein the only lubricant present is a lubricant selected from sodium stearyl fumarate, sodium lauryl sulfate, glyceryl behenates, hydrogenated vegetable oils, wax cetyl esters and talc.

The invention also relates to a pharmaceutical composition in the form of a tablet comprising
(a) up to 10% by weight mono-fumarate of (R)-3-(6-(4-methylphenyl)-pyridin-3-yloxy)-1-aza-bicyclo[2.2.2]octane as active ingredient (e.g. from 0.1 to 3% by weight, e.g. about 0.7% by weight);
(b) a filler comprising maize starch (e.g. from 1 to 20% by weight, e.g. about 13% by weight); microcrystalline cellulose (e.g. from 15 to 35% by weight, e.g. about 25% by weight); and sprayed lactose (e.g. from 40 to 75% by weight, e.g. about 68% by weight);
(c) a disintegrant comprising sodium carboxymethylcellulose XL (e.g. from 0.5 to 5% y weight, e.g. about 2% by weight);
(d) a lubricant (e.g. from 0.5 to 3% by weight, e.g. about 1.5% by weight); and
(e) a gliding agent comprising Aerosil (e.g. from 0.1 to 1% by weight, e.g. about 0.5% by weight);
wherein the only lubricant present is sodium stearyl fumarate.

It has been found that tablets comprising mono-fumarate of (R)-3-(6-(4-methylphenyl)-pyridin-3-yloxy)-1-aza-bicyclo[2.2.2]octane in low weight percentages which are manufactured as bilayer tablets are very stable. Such bilayer tablets comprise an active ingredient layer and an auxiliary layer being devoid of the mono-fumarate.

The invention also relates to a pharmaceutical composition in the form of a tablet comprising from 1 to 10% by weight mono-fumarate of (R)-3-(6-(4-methylphenyl)-pyridin-3-yloxy)-1-aza-bicyclo[2.2.2]octane as active ingredient and at least one pharmaceutically acceptable carrier;
wherein the composition comprises an active ingredient layer comprising the mono-fumarate and an auxiliary layer being devoid of the mono-fumarate;
wherein the weight ratio of the active ingredient layer to the auxiliary layer is from 10:90 to 90:10 (e.g. form 20:80 to 50 to 50; e.g. from 20:80 to 40:60; e.g. about 22.5 to 77.5).

The invention also relates to a pharmaceutical composition in the form of a tablet comprising from 1 to 10% by weight mono-fumarate of (R)-3-(6-(4-methylphenyl)-pyridin-3-yloxy)-1-aza-bicyclo[2.2.2]octane as active ingredient (e.g. from 1 to 5% by weight, e.g. from 2 to 4% by weight);
wherein the composition comprises an active ingredient layer comprising the mono-fumarate and an auxiliary layer being devoid of the mono-fumarate;
wherein the weight ratio of the active ingredient layer to the auxiliary layer is from 10:90 to 90:10 (e.g. form 20:80 to 50 to 50; e.g. from 20:80 to 40:60; e.g. about 22.5 to 77.5);
wherein the active ingredient layer comprises
(1a) from 11 to 25% by weight of the active ingredient layer mono-fumarate (e.g. from 11 to 20% by weight of the active ingredient layer, e.g. about 15.5% by weight of the active ingredient layer);
(1b) a filler;
(1c) a disintegrant;
(1d) a lubricant; and
(1e) a gliding agent; and
wherein the auxiliary layer comprises
(2a) a filler;
(2b) a disintegrant;
(2c) a lubricant; and
(2d) a gliding agent.

The invention also relates to a pharmaceutical composition in the form of a tablet comprising from 1 to 10% by weight mono-fumarate of (R)-3-(6-(4-methylphenyl)-pyridin-3-yloxy)-1-aza-bicyclo[2.2.2]octane as active ingredient (e.g. from 1 to 5% by weight, e.g. from 2 to 4% by weight);

wherein the composition comprises an active ingredient layer comprising the mono-fumarate and an auxiliary layer being devoid of the mono-fumarate;

wherein the weight ratio of the active ingredient layer to the auxiliary layer is from 10:90 to 90:10 (e.g. form 20:80 to 50 to 50; e.g. from 20:80 to 40:60; e.g. about 22.5 to 77.5); wherein the active ingredient layer comprises (1a) from 11 to 25% by weight of the active ingredient layer mono-fumarate (e.g. from 11 to 20% by weight of the active ingredient layer, e.g. about 15.5% by weight of the active ingredient layer);

(1b) a filler comprising microcrystalline cellulose (e.g. from 15 to 35% by weight of the active ingredient layer, e.g. about 25% by weight); and sprayed lactose (e.g. from 40 to 70% by weight of the active ingredient layer, e.g. about 53% by weight);

(1c) a disintegrant comprising sodium carboxymethylcellulose XL (e.g. from 1 to 5% by weight of the active ingredient layer, e.g. about 3% by weight);

(1d) a lubricant comprising sodium stearyl fumarate (e.g. from 1 to 5% by weight of the active ingredient layer, e.g. about 3% by weight); and (1e) a gliding agent comprising Aerosil (e.g. from 0.1 to 1% by weight of the active ingredient layer, e.g. about 0.5% by weight); and wherein the auxiliary layer comprises (2a) a filler comprising microcrystalline cellulose (e.g. from 10 to 35% by weight of the auxiliary layer, e.g. about 26% by weight); and sprayed lactose (e.g. from 50 to 75% by weight of the auxiliary layer, e.g. about 69% by weight);

(2b) a disintegrant comprising sodium carboxymethylcellulose XL (e.g. from 1 to 3% by weight of the auxiliary layer, e.g. about 1.9% by weight);

(2c) a lubricant comprising sodium stearyl fumarate (e.g. from 1 to 5% by weight of the auxiliary layer, e.g. about 3% by weight); and (2d) a gliding agent comprising Aerosil (e.g. from 0.1 to 1% by weight of the auxiliary layer, e.g. about 0.5% by weight).

II. Methods to Make Salts of Aza-Bicyclic Di-Aryl Ethers or their Intermediates

The present invention relates also to novel processes for the production of (R)-3-(6-(4-methylphenyl)-pyridin-3-yloxy)-1-aza-bicyclo[2.2.2]octane in free form or in salt form and its direct precursor, 5-chloro-2-(4-methylphenyl)-pyridine.

The compound 5-chloro-2-(4-methylphenyl)-pyridine of the formula II

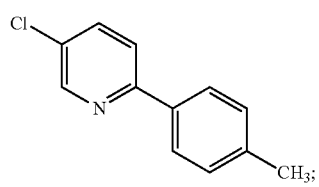

(II)

is a valuable intermediate in the production of (R)-3-(6-(4-methylphenyl)-pyridin-3-yloxy)-1-aza-bicyclo[2.2.2]octane of the formula I

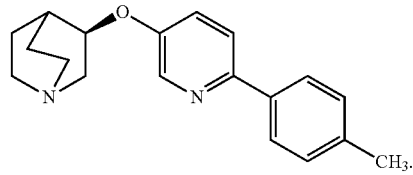

(I)

Both compounds are described in WO2004/022556A1. (R)-3-(6-(4-methylphenyl)-pyridin-3-yloxy)-1-aza-bicyclo[2.2.2]octane has good pharmacological properties and can be used as an α7-nAChR agonist useful in therapy for disorders which respond to α7-nAChR modulation, e.g. neurodegenerative (e.g. Alzheimers Disease) and/or psychiatric (e.g. schizophrenia) disorders. Depending on indication/patient population size, pharmaceuticals may be produced in large quantities. For example, the blood pressure medicament valsartan (being sold as Diovan™) is produced in quantities of several hundred metric tons per annum.

WO2004/022556A1 discloses a process for the production of 5-chloro-2-(4-methylphenyl)-pyridine wherein 2-bromo-5-chloropyridine is reacted with 4-methyl-phenylboronic acid in the presence of the base $Na_2CO_3$ and the palladium catalyst tetrakis(triphenylphosphine)palladium (catalyst load being 4.6 mol %) at about pH9.8.

This process has several draw-backs regarding cost-effectiveness for large scale production: a) 2-bromo-5-chloro-pyridine is commercially not readily available and is costly as a starting material; b) the used palladium (0) catalyst tends to gradually degrade on storage and requires strict handling precautions; furthermore because of its sensitivity it is added usually in comparably high loads of about 5 mol % to such reactions; c) the applied high catalyst load results in an unacceptably high levels of residual palladium in the crude reaction product, because this compound itself is a good palladium ligand, and additional costly purification operations are required (e.g. chromatography and/or treatment with palladium complexing agents); d) an uneconomically high dilution of 0.40 (w/w) % (mass percentage) is applied in order to subdue competing side reactions at the required elevated temperatures of 75-100° C.; and e) the reaction conditions are associated with slow starting material conversion rates which may result in incomplete conversion even after 24 hours; thus parallel progression of catalyst deactivation/competing side reactions may further contribute to high production costs due to lost yield and additional purification efforts.

WO2004/022556A1 also discloses a process for the production of (R)-3-(6-(4-methylphenyl)-pyridin-3-yloxy)-1-aza-bicyclo[2.2.2]octane wherein 5-chloro-2-(4-methylphenyl)-pyridine is reacted with (R)-1-aza-bicyclo[2.2.2]octan-3-ol by heating in the presence of the base sodium hydride using dimethylformamide as solvent.

This process is not well-suited for industrial scale up because heating of sodium hydride in the presence of solvents like dimethylformamide is known to be unsafe and may lead to hazardous run-away conditions.

The aim of the invention is therefore to provide novel processes for the production of the di-aryls 5-chloro-2-(4-methylphenyl)-pyridine and (R)-3-(6-(4-methylphenyl)-pyridin-3-yloxy)-1-aza-bicyclo[2.2.2]octane which make it possible to prepare said compounds in high yields and good quality in an economically advantageous and easily handled way.

The processes according to the present invention are summarized in Scheme 1.

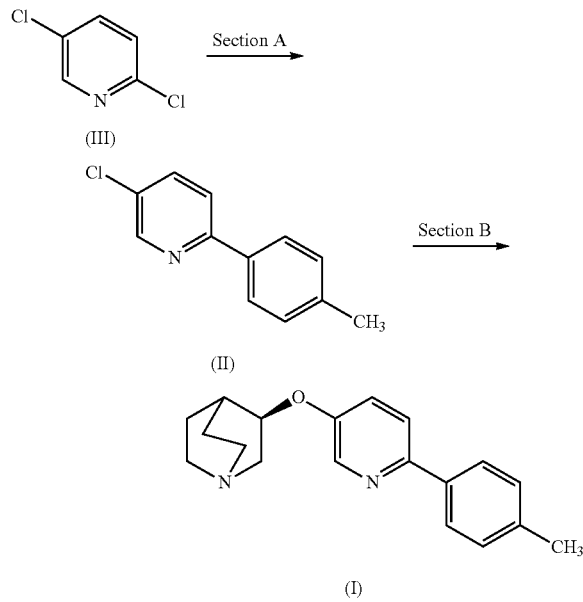

Namely, a compound of formula (III) is converted into a compound of formula (I), or a salt thereof, comprising a) any one of the methods in Section A to convert the compound of formula (III) into a compound of formula (II) or a salt thereof; and b) any one of the methods in Section B to convert the compound of formula (II) or the salt thereof into the compound of formula (I), or a salt thereof.

Sections A and B as such are also preferred embodiments of the present invention.

The invention specially relates to the processes described in each section. The invention likewise relates, independently, to every single step described in a process sequence with the corresponding section. Therefore, each and every single step of any process, consisting of a sequence of steps, described herein is itself a preferred embodiment of the present invention.

It is noted that explanations made in one section are also applicable for other sections, unless otherwise stated.

Section A:

In Section A, the present invention relates to a process for the production of a compound of formula II or a salt thereof

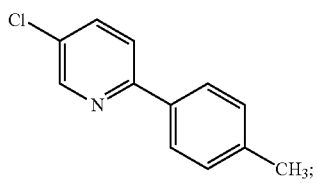

comprising
a) reacting a compound of formula III

(III)

Cl—⟨pyridine⟩—Cl;

with a compound of formula IV (IV)

OH
|
HO—B—⟨phenyl⟩—CH₃;

and/or
with a compound of formula IVA (IVA)

$M_1 \left[ \begin{array}{c} OH \\ HO\text{-}B \\ HO \end{array} \text{—}\langle phenyl\rangle\text{—}CH_3 \right]_n;$ wherein $M_1$ is alkali and n is 1 or $M_1$ is earth alkali and n is 2; in the presence of a palladium catalyst; a base selected from a carbonate base, a phosphate base, a hydroxide base and an alcoholate base; water and an inert solvent;
to form the compound of formula II; and
b) optionally converting the compound of formula II to a salt thereof.

Reaction Step a)

In one embodiment of the process of Section A, compounds of formula II in free base form are produced.

The compound of formula III is readily commercially available. This starting compound is distinguished from the corresponding prior art starting compound (i.e. 2-bromo-5-chloropyridine) by being especially readily accessible and economical. It is known, however, that, under the conditions of palladium-catalysed Suzuki-coupling, this class of starting compounds, the 2-chloro-pyridines, are more difficult to couple with high yield/good purity, because of the lower reactivity of the chlorine leaving group, compared to bromo-analogs. As the invention makes those starting compounds accessible to the palladium-catalysed Suzuki-coupling in high yield/good purity, the process of Section A is especially interesting from an economic point of view. Furthermore, low palladium catalyst loads of <1 mol % may be used.

The compound of formula IV is readily commercially available. In one embodiment of the process of Section A, a compound of formula IV is used.

The term "alkali" in compounds of formula IVA refers typically to sodium or potassium; the term "earth alkali" refers typically to magnesium or calcium. Compounds of formula IVA are accessible according to known methods (e.g. Organic letters (8), 2006, 4071-4074 and cited references therein). In one embodiment of the process of Section A, a compound of formula IVA is used.

In the process of Section A, compounds of formula III can be used typically in mass percentages of between 0.5 (w/w) % and 10 (w/w) %. More preferably, compounds of formula III are used in mass percentages between 2.5 (w/w) % and 8 (w/w) %. Even more preferably, compounds of formula III are used in mass percentages between 4.5 (w/w) % and 6.5 (w/w) %, e.g. about 5.1 (w/w) %. The possibility of using high mass percentages/concentrations of compounds of formula III is an important advantage of the process according to the invention as with high concentrations of starting materials less solvent is needed, which makes the process according to the invention especially suitable for industrial-scale production.

Mass percentages (w/w) % are calculated by division of the mass of the compound in question with the mass of the total reaction mixture (prior to workup) and multiplied by 100.

In the process of Section A, compounds of formula IV or compounds of formula IVA are typically used in equimolar amounts or in excess relative to compounds of formula III, preferably in an up to 2-fold excess, especially in an up to 1.5-fold excess, more especially in an up to about 1.1-fold excess. In one embodiment, compounds of formula IV are used in an about 1.1-fold excess.

In the process of Section A, the palladium catalyst typically is (but not limited to)
(a) a palladium (0)- or palladium (II)-triarylphosphine or palladium (II)-bisdiphenyl complex optionally in the presence of additional amounts of a triarylphosphine ligand, or
(b) a palladium (II) salt in the presence of a mono- or bisdentate arylphosphine ligand, or
(c) metallic palladium, optionally deposited on a support, in the presence of triarylphosphine.

Such catalysts are well known; see, e.g. Angewandte Chemie (105), 1993, 1589ff; or Tetrahedron (58), 2002, 9633ff.

Of the palladium complexes having palladium in the oxidation state 0, tetrakis(triphenyl-phosphine)palladium and tetrakis[tri(o-tolyl)phosphine)palladium are particularly suitable.

Of the palladium complexes having palladium in the oxidation state +2, di-(triphenyl-phosphine)palladium(II) acetate $(Pd(O_2CCH_3)_2([C_6H_5]_3P)_2)$, di-(triphenyl)phosphine)-palladium(II) chloride $(PdCl_2([C_6H_5]_3P)_2)$, and e.g. 1,1'-bis-(diphenylphosphine)ferrocene palladium (II) chloride $(PdCl_2(dppf))$ are particularly suitable.

In one embodiment of the invention, the palladium catalyst is di-(triphenylphosphine)-palladium(II) chloride.

It is understood that the reactivity of the arylhalogen component in the catalytic cycle of the cross coupling reaction can be fine-tuned with Pd-catalysts containing special, less readily available ligands. The preferred scope of the invention is on commercially readily available and air-stable Pd(II) catalysts.

A palladium(II) salt employed in the presence of a triarylphosphine ligand, for example a triphenylphosphine or tri(o-tolyl)phosphine ligand, is suitably palladium(II) acetate or palladium dichloride.

Typically, from 2 to 6 equivalents of the triarylphosphine ligand is complexed with one equivalent of the palladium salt or additionally used with the palladium-triarylphosphine complex.

Metallic palladium is preferably used as a powder or on a support, for example, as palladium on activated carbon, palladium on aluminium oxide, palladium on barium carbonate, palladium on barium sulphate, palladium on calcium carbonate, palladium on aluminium silicates such as montmorillonite and palladium on silic, in each case having a palladium content of 0.5 to 12% by weight. Such supported catalysts may additional contain further doping substances, for example, lead.

When using supported metallic palladium catalysts, the simultaneous use of a complexed ligand, of the type discussed above, is beneficial, particularly the use of palladium on activated carbon in the presence of triphenylphosphine, tri(o-tolyl)phosphine or other triarylphosphine as complexed ligand, the aryl groups being suitably substituted with 1 to 3 sulphonate groups. Suitably, 2 to 3 equivalents of these ligands are used for each equivalent of palladium metal.

In the process of Section A, the palladium catalyst is typically employed in a ratio of from 0.01 to 10 mol %, preferably from 0.05 to 3 mol % and especially from 0.1 to 1 mol %, based on the amount of the compound of formula III. In one embodiment, the palladium catalyst is employed in a ratio of 0.6 mol %, based on the amount of the compound of formula III.

Suitable carbonate bases for the process of Section A are e.g. alkali or earth alkali carbonates, e.g. $Na_2CO_3$, $K_2CO_3$ or $Cs_2CO_3$; preferably $K_2CO_3$ or $Cs_2CO_3$. Suitable phosphate bases for the process of Section A are e.g. $K_3PO_4$. Suitable hydroxide bases for the process of Section A are e.g. NaOH or KOH. Suitable alcoholate bases for the process of Section A are e.g. e.g. sodium tert-butanolate, potassium tert-butanolate, sodium methanolate or sodium ethanolate.

In one embodiment, preference is given to phosphate bases and special preference is given to $K_3PO_4$.

Suitable amounts of base for the process of Section A are, for example, from 1.5 to 4 equivalents, especially from 2 to 3 equivalents relative to compounds of formula III. In one embodiment, about 3 equivalents relative to compounds of formula III are used. It is noted that processes of Section A using compounds of formula IVA require less base than processes using compounds of formula IV only.

The process of Section A is carried out in the presence of water. Typically a mass percentage from 35 (w/w) % to 65 (w/w) % water is present in the reaction mixture; preferably from 40 (w/w) % to 55 (w/w) %. In one embodiment, about 54 (w/w) % water is present.

The process of Section A is carried out typically at a pH from 10.5 to 13, preferably from 11 to 12.5, more preferably at 11.5 to 12. It is understood that the pH-range given represents the average pH over the whole reaction volume at any given time, whereas local pH values may be transiently different (e.g. directly at the base addition site).

Carrying out the process of Section A at the intended pH is typically achieved by slow addition of the base, preferably (but not limited to) as an aqueous base solution. Slow addition of the base can be done portion-wise or continuously. It is understood that the pKa of the added base or the pH of the added aqueous base-solution will limit the maximal obtainable pH in the aqueous reaction mixture. During slow addition of base, the pH in the aqueous reaction mixture will rise gradually, e.g. when using one equivalent of 4-methyl-phenylboronic acid, the first equivalent of base may lead to an increase from approximately pH 2.5 (which may correspond to the pH of the boronic acid in the aqueous reaction mixture) to approximately pH 10 where the base consuming cross coupling reaction starts and the pH may be further increased/maintained by further addition of base.

The process of Section A is carried out in the presence of an inert solvent. Said inert solvents typically have a boiling point above 60° C. Examples of said inert solvents are alcohols, e.g. isopropanol; ethers; ketones; amides; aromatic hydrocarbons; or mixtures of such solvents. Preference is given to partly water soluble solvents, such as e.g. tetrahydrofurane or isopropanol, as in the course of the reaction these solvents separate as a product containing organic layer from the salt rich aqueous layer and are particularly convenient for the work-up operations. In one embodiment, the inert solvent is tetrahydrofuran; typically used in a mass percentage of about 15 (w/w) %.

The process of Section A is carried out in a temperature range from ambient temperature to elevated temperature; preferably in a temperature range from 30° C. to 100° C., especially in a temperature range from 35° C. to 60° C.

The reaction time of the process of Section A is generally from 0.5 to 24 hours, preferably from 1 to 10 hours, especially from 2 to 5 hours.

The process of Section A may be carried out in an inert gas atmosphere. For example, nitrogen or argon is used as inert gas.

The process of Section A can be carried out at normal pressure, but is not limited to this pressure.

In a preferred embodiment, the process of Section A comprises a work-up in which cysteine (e.g. L-cysteine or racemic cysteine) is added to the biphasic reaction mixture to form a water soluble palladium cysteine complex. This complex is removed from the product containing organic phase by separation of the aqueous phase from the non-aqueous phase and thus ensures a high product quality of the compound of formula II with regard to residual palladium. The rate of complex formation is particularly fast and therefore advantageous with regard to process costs with preferably used partly water soluble solvents, such as tetrahydrofurane or isopropanol, while with more lipophilic solvents, such as toluene or xylene, complexation rates are slower.

Consequently, one embodiment of the process of Section A is a process for the production of a compound of formula II or a salt thereof comprising a1) reacting a compound of formula III with a compound of formula IV and/or a compound of formula IVA in the presence of a palladium catalyst; a base selected from a carbonate base, a phosphate base, a hydroxide base and an alcoholate base; water and an inert, partly water soluble solvent;

a2) adding cysteine to the biphasic reaction mixture after formation of the compound of formula II;

a3) separating the phases;

a4) isolating the compound of formula II from the non-aqueous phase; and b) optionally converting the compound of formula II to a salt thereof.

Reaction Step b)

The compound of the formula II may be converting to its salt either after isolation of the compound of the formula II as a free base in solid form or by addition of a suitable salt forming agent to a solution comprising the compound of the formula II.

An example of a suitable salt forming agent is HCl.

In one embodiment of the process of Section A, the present invention relates to a process for the production of a compound of formula II comprising a) reacting a compound of formula III
with a compound of formula IV
in the presence of the palladium catalyst di-(triphenylphosphine)palladium(II) chloride; the phosphate base $K_3PO_4$; water and an inert solvent;

wherein compounds of formula III are used in mass percentages between 4.5 (w/w) % and 6.5 (w/w) %;

wherein the palladium catalyst is employed in a ratio of from 0.1 to 1 mol %, based on the amount of the compound of formula III;

wherein from 2 to 3 equivalents of phosphate base relative to compounds of formula III are used;

wherein a mass percentage from 40 (w/w) % to 55 (w/w) % water is present in the reaction mixture; and wherein the reaction is carried out at a pH from 11.5 to 12; to form the compound of formula II.

Section B:

In Section B, the present invention relates to a process for the production of a compound of formula I

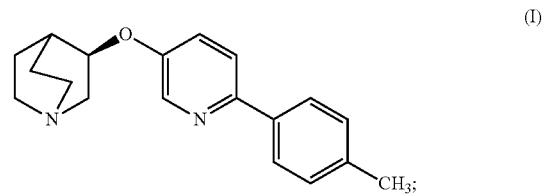 [SMILES: Cc1ccc(-c2ccc(O[C@H]3CN4CCC3CC4)cn2)cc1]

or a salt thereof comprising c) reacting a compound of formula II

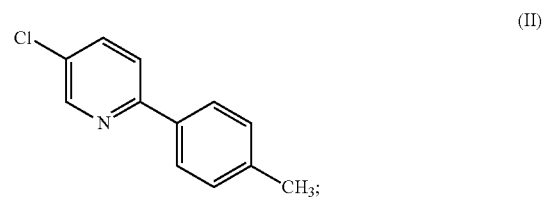 [SMILES: Cc1ccc(-c2ccc(Cl)cn2)cc1]

or a salt thereof;
with a compound of formula V

or a salt thereof;
at elevated temperature in the presence of a base and an inert dipolar aprotic solvent;

wherein the base is $(M_2)OC(R)_3$, wherein $M_2$ is sodium or potassium and each R independently is $C_{1-6}$alkyl or two R together with the carbon atom they are bound to form $C_4$-$C_6$cycloalkyl, or the base is a hydroxide base;

to form the compound of formula I; and d) optionally converting the compound of formula I to a salt thereof.

Reaction Step c)

The compound of formula II can be made as described in Section A or e.g. according to WO2004/022556A1. In one embodiment of the process of Section B the compound of formula II is used in free base form.

The compound of formula V is commercially readily available. In one embodiment of the process of Section B the compound of formula V is used in free base form.

In the process of Section B, compounds of formula II can be used typically in mass percentages of between 1 (w/w) % and 15 (w/w) %. More preferably, compounds of formula II are used in mass percentages of between 3 (w/w) % and 10 (w/w) %. Even more preferably, compounds of formula II are used in mass percentages of between 5 (w/w) % and 9 (w/w) %; e.g. 7.9 (w/w) %.

In the process of Section B, compounds of formula V are typically used in equimolar amounts or in excess relative to compounds of formula II, preferably in an up to 3-fold excess, especially in an up to 2-fold excess, more especially in an up to 1.1-fold to 1.5-fold excess. In one embodiment, compounds of formula V are used in an about 1.3-fold excess.

In one embodiment of the process of Section B, the base is $(M_2)OC(R)_3$, wherein $M_2$ is sodium or potassium and each R independently is $C_{1-6}$alkyl or two R together with the carbon atom they are bound to form $C_{4-8}$cycloalkyl. In one embodiment, the base is $(M_2)OC(R)_3$, wherein $M_2$ is sodium or potassium and each R independently is $C_{1-4}$alkyl. In one embodiment, the base is $(M_2)OC(R)_3$, wherein $M_2$ is sodium or potassium and each R independently is $C_{1-2}$alkyl. In one embodiment, the base is sodium tert-butanolate or potassium tert-butanolate. In one embodiment, the base is potassium tert-butanolate.

In one embodiment of the process of Section B, the base is a hydroxy base, e.g. NaOH or KOH.

Suitable amounts of base for the process of Section B are, for example, from 1 to 2 equivalents, especially from 1 to 1.5 equivalents relative to compounds of formula II. In one embodiment, about 1.1 equivalents relative to compounds of formula II are used. It is noted that when salts of compounds of formula II are used, e.g. a hydrochloride salt, an appropriate higher amount of base will become necessary for performing the process.

Suitable inert dipolar aprotic solvents for the process of Section B are e.g. dimethylsulfoxide (DMSO), dimethylacetamide (DMAC), dimethylformamide (DMF) or N-methylpyrrolidone (NMP). In one embodiment, the dipolar aprotic solvent is DMSO, typically in a mass percentage of about 75-90 (w/w) % of the reaction mixture.

The reaction mixture for the process of Section B may further comprise an inert lipophilic co-solvent having a boiling point above 100° C., preferably toluene or xylene. In one embodiment, the reaction mixture comprises a DMSO/toluene solvent/co-solvent mixture, said mixture typically present in a mass percentage of about 70-85 (w/w) % with a DMSO/toluene ratio of from 5:0.1 to 2:3 by weight, preferably in a ratio of about 3:2 by weight.

In the process of Section B additional solvents may be used, e.g. if the alcoholate base is added as a solution, such as e.g. in tetrahydrofurane solution. In one embodiment, tetrahydrofurane is used as the solvent for the base. Said additionally added solvent may be distilled off before any or any substantive formation of compounds of formula I takes place, e.g. before the intended elevated temperature for performing the process of Section B is reached, typically between 80° C. and 130° C., and/or before addition of compounds of formula II.

The process of Section B is typically carried out substantially water-free. In one embodiment, the reaction according to the invention is carried out in the presence of maximally about 5 mol % water relative to compounds of formula II. A typical way to remove water from the reaction mixture is distillation after base addition and/or before the intended elevated temperature for performing the process of Section B is reached.

The process of Section B is carried out at elevated temperature; preferably in a temperature range from 80° C. to 130° C., especially in a temperature range from 90° C. to 120° C., more especially in a temperature range from 100° C. to 105° C.

The reaction time of the process of Section B is generally from 0.5 to 24 hours, preferably from 1 to 10 hours, especially from 2 to 5 hours.

The process of Section B may be carried out in an inert gas atmosphere. For example, nitrogen or argon is used as inert gas.

The process of Section B can be carried out at normal pressure, but is not limited to.

In the process described in WO2004/022556A1, the base is added in an amount of 1.2 equivalents relative to compounds of formula II to compounds of formula V. Then the compound of formula II is added to the reaction mixture. There is no further addition of base to the reaction mixture. With such procedural steps, the full amount of base (i.e. 1.2 equivalents) is already present when compound of formula II react with compounds of formula V, i.e. the base is not added gradually.

It is an important finding of the invention that yield and side-product profile are improved when less base is initially present and when the base is gradually added.

Consequently, embodiment B1 of the process of Section B is a process for the production of a compound of formula I or a salt thereof comprising c) reacting a compound of formula II or a salt thereof with a compound of formula V or a salt thereof;
at elevated temperature in the presence of a base and an inert dipolar aprotic solvent;
wherein the base is $(M_2)OC(R)_3$, wherein $M_2$ is sodium or potassium and each R independently is $C_{1-6}$alkyl or two R together with the carbon atom they are bound to form $C_{4-6}$cycloalkyl, or the base is a hydroxide base;
and wherein the base is gradually added to the reaction mixture;
to form the compound of formula I; and
d) optionally converting the compound of formula I to a salt thereof.

One way to carry out embodiment B1 is e.g. the formation of a mixture comprising compounds of formula II or salts thereof and compounds of formula V or salts thereof, wherein no base is present; and adding the base to said mixture with a relatively low flow rate.

In one embodiment of embodiment B1, in step c):
c1) a mixture is formed, which comprises the compound of formula II or the salt thereof; the compound of formula V or the salt thereof; and maximally about 0.5 equivalents of the base relative to compounds of formula II; and
c2) base is gradually added to said mixture;

In one embodiment of embodiment B1, in step c1) the mixture comprises maximally about 0.3 equivalents, preferably maximally about 0.1 equivalents, of the base relative to compounds of formula II.

In one embodiment, in step c1) the mixture comprises substantially no base.

In one embodiment, in step c1) the mixture comprises no base.

In one embodiment of embodiment B1, in step c2) base is added gradually by (i) adding with a flow rate of maximally about 3.8 mol % relative to compounds of formula II per minute until about 1.1 equivalents relative to compounds of formula II are added to the mixture or by (ii) adding portion-wise wherein the initial portion is maximally 0.5 equivalents, preferably 0.25 equivalents, relative to compounds of formula II.

In one embodiment of embodiment B1, in step c2) base is added gradually by adding with a flow rate of maximally about 1.3 mol % relative to compounds of formula II per minute until about 1.1 equivalents relative to compounds of formula II are added to the mixture.

In one embodiment of embodiment B1, in step c2) base is added gradually by adding with a flow rate that the added base is rapidly consumed for the formation of the compound of formula I and an inorganic salt, e.g. potassium chloride, preferably, but not limited to, until the sum of base from step c1) and c2) is about 1.1 equivalents relative to compounds of formula II.

Reaction Step d)

The compound of the formula I may be converting to its salt either after isolation of the compound of the formula I as a free base in solid form or by addition of a suitable salt forming agent to a solution comprising the compound of the formula I.

An example of a suitable salt forming agent is fumaric acid.

In one embodiment, fumaric acid is added directly to the reaction mixture of step c), generally after formation of the compounds of formula I and a hydrolytic work-up.

In one embodiment of the process of Section B, the present invention relates to a process for the production of a compound of formula I or a salt thereof comprising
c) reacting a compound of formula II with a compound of formula V at a temperature range from 80° C. to 130° C. in the presence of 1 to 1.5 equivalents of base relative to compounds of formula II; and an inert dipolar aprotic solvent; wherein the base is selected from sodium tert-butanolate and potassium tert-butanolate; and wherein
c1) a mixture is formed, which comprises the compound of formula II; the compound of formula V; and no base; and
c2) the base is added to said mixture with a flow rate of maximally about 3.8 mol % relative to compounds of formula II per minute until about 1.1 equivalents relative to compounds of formula II are added to the mixture;
to form the compound of formula I; and
d) optionally converting the compound of formula I to a salt thereof.

The following non-limiting examples are illustrative of the disclosure.

REFERENCE EXAMPLE A1

Preparation/Characterization of free base of (R)-3-(6-(4-methylphenyl)-pyridin-3-yloxy)-1-aza-bicyclo[2.2.2]octane in crystalline form (Form A)

About 8 mg of (R)-3-(6-(4-methylphenyl)-pyridin-3-yloxy)-1-aza-bicyclo[2.2.2]octane in free base form dissolved in 0.2 ml methanol was dried in vacuum at 40° C. for >5 hours. After drying, acetonitrile was added to the solid residue and the mixture was heated to 40° C. and vortexed for about 2 hours. The mixture was dried and the remaining solid was analyzed by XPRD.

Following this method, a pattern as shown in FIG. 7A (Form A) can be obtained.

Form A of the free base shows low solubility in aqueous media (0.05 mg/ml).

It is hygroscopic: when tested, Loss on drying (LOD) of a sample was 0.1% and moisture gain was 2% at 93% relative humidity (RH).

Its melting point was determined by heating at 2° C./minute to be 106° C. (onset) with subsequent decomposition.

REFERENCE EXAMPLE A2

Preparation/Characterization of free base of (R)-3-(6-(4-methylphenyl)-pyridin-3-yloxy)-1-aza-bicyclo[2.2.2]octane in crystalline form (Form B)

About 8 mg of (R)-3-(6-(4-methylphenyl)-pyridin-3-yloxy)-1-aza-bicyclo[2.2.2]octane in free base form dissolved in 0.2 ml methanol was dried in vacuum at 40° C. for >5 hours. After drying, ethanol was added to the solid residue and the mixture was heated to 40° C. and vortexed for about 2 hours. The mixture was dried and the remaining solid was analyzed by XPRD (see FIG. 7B, Form B).

The same experiment was performed using ethanol or isopropanol as solvent. Basically the same XPRD pattern was obtained. As all three solid forms gained an XPRD pattern as described under Reference Example A1 upon further drying, it was concluded that this new form is an alcohol solvate with low association temperature.

EXAMPLE 1

Preparation of mono-fumarate salt of (R)-3-(6-(4-methylphenyl)-pyridin-3-yloxy)-1-aza-bicyclo[2.2.2]octane in crystalline form 500 mg of (R)-3-(6-(4-methylphenyl)-pyridin-3-yloxy)-1-aza-bicyclo[2.2.2]octane in free base form were suspended in 20 ml isopropyl alcohol. A stoichiometric amount of fumaric acid was added. The resulting solution was stirred at ambient temperature for 14 hours. The precipitate was collected by filtration and analyzed by proton-NMR and XRPD (see FIG. 1). Yield was 85%. Analysis of proton-NMR confirmed salt formation, a base/acid ratio of about 1:1 and the fact that the salt was not a solvate.

EXAMPLE 1.1

Preparation of mono-fumarate salt of (R)-3-(6-(4-methylphenyl)-pyridin-3-yloxy)-1-aza-bicyclo[2.2.2]octane in crystalline form by seeded crystallization a) Preparation 7.3 g mono-fumarate of (R)-3-(6-(4-methylphenyl)-pyridin-3-yloxy)-1-aza-bicyclo[2.2.2]octane (purity >98%; prepared as described e.g. in Example 13.2) was dissolved in ethanol (42.9 g)/isopropanol (8.5 g)/water (7.2 g) at about 50° C., clarified by filtration and added at this temperature gradually over a period of about 8 hours to filtered tertiary-butyl-methylether (118.4 g) at a temperature of about 50° C. After about 25% of the filtrate was added, an ultrasonificated suspension of seed crystals of the mono-fumarate of (R)-3-(6-(4-methylphenyl)-pyridin-3-yloxy)-1-aza-bicyclo[2.2.2]octane (6 mg, prepared e.g. as described in Example 13.2) in isopropanol (0.1 ml) was added to induce crystallization. The product suspension was maintained for another 1 hour at 50° C. and cooled to 0° C. within 8 hours. After another 1 hour at this temperature the solids were isolated by filtration, washed with isopropanol/tertiary-butylmethylether (40 ml, 1:1 mixture) and dried at about 50° C. under reduced pressure to yield the mono-fumarate of (R)-3-(6-(4-methylphenyl)-pyridin-3-yloxy)-1-aza-bicyclo[2.2.2]octane (5.85 g; 81% of theory; purity >99.5%).

b) Characterization: Particle Size Measurements by Fraunhofer Light Diffraction

Result:

Mono-fumarate salt of (R)-3-(6-(4-methylphenyl)-pyridin-3-yloxy)-1-aza-bicyclo[2.2.2]octane in crystalline form prepared as described according to Example 1.1 was tested. The following values were obtained: $X_{10}$=5.6±0.5 µm; $X_{50}$=26.8±1.3 µm and $X_{90}$=77.3±3.3 µm (N=8).

Procedure:

To about 0.5 g of test substance add some drops of the dispersing aid (1% Octastat 5000 (Octel Corp.) in white spirit (Sangajol, Schweizerhall Chemie)). Mix intensively on a vortex mixer, in order to wet the substance thoroughly and to form a smooth and homogeneous paste. Dilute the paste with white spirit to a final volume of 3-6 ml and mix the dispersion again. Determine the cumulative volume distribution using a laser diffraction instrument, e.g. determine the particle sizes at the undersize values of 10%, 50% and 90% ($x_{10}$, $x_{50}$, $x_{90}$). Measuring device: Sympatec HELOS (Sympatec GmbH; focal length: 500 mm, optical concentration ≥5%, duration of measurement: 40 sec).

Dispersion device: Suspension cell (QUIXEL, Sympatec GmbH).

EXAMPLE 2

Preparation of mono-maleate salt of (R)-3-(6-(4-methylphenyl)-pyridin-3-yloxy)-1-aza-bicyclo[2.2.2]octane in crystalline form 500 mg of (R)-3-(6-(4-methylphenyl)-pyridin-3-yloxy)-1-aza-bicyclo[2.2.2]octane in free base form were suspended in 5 ml acetonitrile. A stoichiometric amount of maleic acid was added. The resulting solution was stirred at ambient temperature for 14 hours. The precipitate was collected by filtration and analyzed by proton-NMR and XRPD (see FIG. 2). Yield was 63%. Analysis of proton-NMR confirmed salt formation, a base/acid ratio of about 1:1 and the fact that the salt was not a solvate.

EXAMPLE 3

Preparation of mono-hydrochloride salt of (R)-3-(6-(4-methylphenyl)-pyridin-3-yloxy)-1-aza-bicyclo[2.2.2]octane in crystalline form A 1 L reactor, equipped with a mechanical stirrer, digital thermometer, nitrogen inlet-outlet, reflux condenser and heating mantle was charged with 14.4 g (R)-3-quinuclidinol, 176 g (160 mL) dimethylsulfoxide and 69.5 g (78 mL) 20 wt % potassium tert-butoxide in tetrahydrofuran. The mixture was stirred at 23° C. for 15 minutes and then heated to 95-110° C. over a period of 1 hour to distill off about 40 mL of tetrahydrofuran. Distilling was continued at 110° C. for 30 minutes. The mixture was cooled to 90° C. over a period of 20 minutes. Portionwise, 21 g 5-chloro-2-p-tolylpyridine was added. 11 g (20 mL) dimethylsulfoxide was added. The reaction mixture was heated to 100° C. over a period of 20 minutes and kept at said temperature for 3 hours. The mixture was cooled to 15° C. over a period of 1 hour.

370 g (500 mL) tert-butyl methyl ether was added. 250 g water was added over a period of 30 minutes, while maintaining the temperature below 25° C. The mixture was stirred for 30 minutes. The layers were separated and a solution of 102 g 20% (v/v) aqueous sodium chloride was added to the organic layer. The mixture was stirred for 15 minutes and the layers were separated. The organic layer was filtered.

A 1 L reactor, equipped with a mechanical stirrer, digital thermometer, addition funnel, nitrogen inlet-outlet, reflux condenser and heating mantle was charged with the above organic layer. 109 g (120 mL) peroxide-free 2-propanol was added. A solution of 16.5 g (17.8 mL) 5.3 N HCl in 2-propanol was added over a period of 40 minutes. The mixture was heated to 53° C. and stirred for 30 minutes. The mixture was cooled to 23° C. over a period of 30 minutes and stirred for 1 hour. The solid was collected by filtration and washed with a solution of 2×37 g (50 mL) of 1% (v/v) peroxide-free 2-propanol/tert-butyl methyl ether. The solid was dried at 55° C. under reduced pressure to afford 20.9 g of the mono-hydrochloride salt of (R)-3-(6-(4-methylphenyl)-pyridin-3-yloxy)-1-aza-bicyclo[2.2.2]octane. The material was analyzed by XRPD (see FIG. 3).

EXAMPLE 4.1

Preparation of mono-phosphate salt of (R)-3-(6-(4-methylphenyl)-pyridin-3-yloxy)-1-aza-bicyclo[2.2.2]octane in crystalline form (Form A)

500 mg of (R)-3-(6-(4-methylphenyl)-pyridin-3-yloxy)-1-aza-bicyclo[2.2.2]octane in free base form were suspended in 20 ml ethanol. A stoichiometric amount of phosphoric acid was added. The resulting solution was stirred at ambient temperature for 14 hours. The precipitate was collected by filtration and analyzed by proton-NMR and XRPD (see FIG. 4A, Form A). Yield was 77%. Analysis of proton-NMR confirmed salt formation and the fact that the salt was not a solvate. Elemental analysis was performed confirming a base/acid ratio of about 1:1 (C, 57.9% (58.1%); H, 6.7% (6.4%); N, 7.1% (7.1%); and P, 7.7% (7.9%); theoretical values in brackets).

EXAMPLE 4.2

Preparation of phosphate salt of (R)-3-(6-(4-methylphenyl)-pyridin-3-yloxy)-1-aza-bicyclo[2.2.2]octane in crystalline form (Form B)

About 2.3 mg of (R)-3-(6-(4-methylphenyl)-pyridin-3-yloxy)-1-aza-bicyclo[2.2.2]octane in free base form was dissolved in 0.15 ml ethanol. A stoichiometric amount of phosphoric acid was added. The mixture was dried in vacuum at 40° C. for >5 hours. After drying, 0.1 ml ethanol and 0.05 ml water were added. The mixture was heated to 40° C. and vortexed for about 2 hours. The mixture was dried and the remaining solid was analyzed by XPRD (see FIG. 4B, Form B).

EXAMPLE 4.3

Preparation of phosphate salt of (R)-3-(6-(4-methylphenyl)-pyridin-3-yloxy)-1-aza-bicyclo[2.2.2]octane in crystalline form (Form C)

200 mg of (R)-3-(6-(4-methylphenyl)-pyridin-3-yloxy)-1-aza-bicyclo[2.2.2]octane in free base form was suspended in 2 ml ethanol. One-third of the stoichiometric amount of phosphoric acid was added. The slurry obtained was stirred at ambient temperature and held for 14 hours. Solids were separated by filtration and analyzed by XPRD (see FIG. 4C, Form C).

EXAMPLE 5.1

Preparation of mono-succinate salt of (R)-3-(6-(4-methylphenyl)-pyridin-3-yloxy)-1-aza-bicyclo[2.2.2]octane in crystalline form (Form A)

500 mg of (R)-3-(6-(4-methylphenyl)-pyridin-3-yloxy)-1-aza-bicyclo[2.2.2]octane in free base form were suspended in 5 ml ethanol. A stoichiometric amount of succinic acid was added. The resulting solution was stirred at ambient temperature for 14 hours. The precipitate was collected by filtration and analyzed by proton-NMR and XRPD (see FIG. 5, Form A). Yield was 64%. Analysis of proton-NMR confirmed salt formation, a base/acid ratio of about 1:1 and the fact that the salt was not a solvate.

EXAMPLE 5.2

Preparation of anhydrous mono-succinate salt of (R)-3-(6-(4-methylphenyl)-pyridin-3-yloxy)-1-aza-bicyclo[2.2.2]octane in crystalline form When the Form A of the mono-succinate salt (see Example 5.1) was subjected to heat (under nitrogen) from 25° C. to 115° C., an anhydrous form of mono-succinate salt was observed and analyzed by XRPD (see FIG. 5, Form B).

EXAMPLE 6

Preparation of mono-malonate salt of (R)-3-(6-(4-methylphenyl)-pyridin-3-yloxy)-1-aza-bicyclo[2.2.2] octane in crystalline form 500 mg of (R)-3-(6-(4-methylphenyl)-pyridin-3-yloxy)-1-aza-bicyclo[2.2.2]octane were suspended in 5 ml acetonitrile. A stoichiometric amount of malonic acid was added. The resulting solution was stirred at ambient temperature for 14 hours. The precipitate was collected by filtration and analyzed by proton-NMR and XRPD (see FIG. 6). Yield was 77%. Analysis of proton-NMR confirmed salt formation, a base/acid ratio of about 1:1 and the fact that the salt was not a solvate.

EXAMPLE 7

Comparison of Physico-Chemical Parameters of Salt Forms

|  | Aqueous solubility [mg/ml] | Initial water content | Hygroscopy @ 85% RH | m.p. | Decomposition temperature | Known Multiple forms |
|---|---|---|---|---|---|---|
| Free Base | 0.05 | 0.1 | ~2 | 106 | 224 | Yes |
| Fumarate | >30 | <0.5 | 0.5 | 164 | 207 | No |
| Maleate | >30 | <0.1 | 0.3 | 154 | 207 | No |
| Hydrochloride, Form A | >30 | ~5 | ~5 | 240 | 262 | Yes |
| Phosphate, Form A | >30 | ~0.5 | 0.2 | 222 | 222 | Yes |
| Succinate | 2-15 | ~4.5 | 0.3 | 113 | 222 | Yes |
| Malonate | >30 | ~0 | 1.3 | 140 | 148 | No |

EXAMPLE 8

Hard Capsules

Hard gelatin capsules, each comprising as active ingredient 0.5, 5 or 25 mg of the mono-fumarate of (R)-3-(6-(4-methylphenyl)-pyridin-3-yloxy)-1-aza-bicyclo[2.2.2]octane can be prepared as follows:

| Ingredient for capsule fill | % (w/w) for 0.5 mg capsules | % (w/w) for 5 mg capsules | % (w/w) for 25 mg capsules |
|---|---|---|---|
| Mono-fumarate of (R)-3-(6-(4-methylphenyl)-pyridin-3-yloxy)-1-aza-bicyclo[2.2.2]octane | 0.46 | 4.65 | 23.23 |
| Lactose monohydrate | 65.24 | 61.05 | 42.47 |
| Microcrystalline cellulose | 25.00 | 25.00 | 25.00 |
| Hypromellose | 2.50 | 2.50 | 2.50 |
| Sodium croscarmellose | 6.00 | 6.00 | 6.00 |
| Colloidal silicon dioxide | 0.30 | 0.30 | 0.30 |
| Magnesium stearate | 0.50 | 0.50 | 0.50 |
| Purified water* | q.s. | q.s. | q.s. |

*removed during processing

Preparation process: Mono-fumarate of (R)-3-(6-(4-methylphenyl)-pyridin-3-yloxy)-1-aza-bicyclo[2.2.2]octane, lactose monohydrate, microcrystalline cellulose, a portion of sodium croscarmellose and hypromellose are dry mixed in a high shear mixer bowl, and granulating fluid (purified water) added. Once the granulation is complete, the wet granules are dried in a fluid bed drier and the dry granules are milled. The remaining sodium croscarmellose and colloidal silicon dioxide are passed through a suitable sieve and added to the dried granular material and blended in a suitable blending shell. This is achieved by co-sieving the sodium croscarmellose and the colloidal silicon dioxide with a portion of the milled granules through a suitable sieve into the blending shell. Similarly, the required amount of sieved magnesium stearate is added to the bulk granule and then mixed in the same blending shell. This final blend is encapsulated into capsules using automated equipment. Weight ratio of capsule fill to empty capsule shells is 2:1.

EXAMPLE 9

Tablets

EXAMPLE 9.1

Film-Coated Tablet

Film-coated tablets containing e.g. 0.5 mg of the mono-fumarate of (R)-3-(6-(4-methylphenyl)-pyridin-3-yloxy)-1-aza-bicyclo[2.2.2]octane may be prepared as follows:

Preparation of Pre-Mix:
Weigh-in mono-fumarate of (R)-3-(6-(4-methylphenyl)-pyridin-3-yloxy)-1-aza-bicyclo[2.2.2]octane (e.g. approx. 0.7%) and maize starch (e.g. approx. 13%), mix in a tumble blender (approx 100-300 rotations), pass through a sieve of approx. 0.25-1.0 mm mesh-size. Mix in a tumble blender (approx. 100-300 rotations).

Preparation of Final Blend:
To above pre-mix add microcrystalline cellulose (e.g. approx. 25%), sprayed lactose (e.g. approx. 68%), sodium-carboxymethylcellulose XL (e.g. approx. 2%) and Aerosil (e.g. approx. 0.5%) and mix in a tumble blender (approx. 100-300 rotations). Pass this mixture through a sieve of approx. 0.5-1.0 mm mesh-size and mix again (approx. 100-300 rotations).

Add the sodium-stearyl-fumarate (e.g. approx. 1.5%) through a handsieve at approx. 0.5-1.0 mm mesh-size and mix in a tumble blender (approx. 30-150 rotations).

Compression:
On a rotary press compress the above final blend to cores of approx. 100 mg, using the dosage specific tooling (e.g. approx. 6 mm, round, curved).

Coating:

Prepare a suspension in water with basic coating premixes black, red, yellow and/or white. Coat the above obtained cores in a perforated coating pan, and dry.

EXAMPLE 9.2

Bilayer Film-Coated Tablet

Bilayer film-coated tablets containing e.g. 2.5 mg of the mono-fumarate of (R)-3-(6-(4-methylphenyl)-pyridin-3-yloxy)-1-aza-bicyclo[2.2.2]octane may be prepared as follows:

Final Active Blend:

Weigh-in mono-fumarate of (R)-3-(6-(4-methylphenyl)-pyridin-3-yloxy)-1-aza-bicyclo[2.2.2]octane coarse (e.g. approx. 15.5%), microcrystalline cellulose (e.g. approx. 25%), sprayed lactose (e.g. approx. 53%), sodium-carboxymethylcellulose XL (e.g. approx. 3%) and Aerosil (e.g. approx. 0.5%) and mix in a tumble blender (approx 100-300 rotations). Pass this mixture through a sieve of approx. 0.5-1.0 mm mesh-size and mix again (approx 100-300 rotations).

Add the Na-stearyl-fumarate (e.g. approx. 3%) through a handsieve at approx. 0.5-10 mm and mix in a tumble blender (approx 30-150 rotations).

Final Placebo Blend:

Weigh-in microcrystalline cellulose (e.g. approx. 26%), sprayed lactose (e.g. approx. 69%), sodium-carboxymethylcellulose XL (e.g. approx. 1.9%) and Aerosil (e.g. approx. 0.5%) and mix in a tumble blender (approx 100-300 rotations). Pass this mixture through a sieve of approx. 0.5-1.0 mm mesh-size and mix again (approx 100-300 rotations).

Add the sodium-stearyl-fumarate (e.g. approx. 3%) through a handsieve at approx. 0.5-1.0 mm and mix in a tumble blender (approx 30-150 rotations).

Compression:

On a rotary press compress the above final blends to a bilayer tablet-core of approx. 100 mg with one placebo layer (approx. 77.5 mg) and one active layer (approx. 22.5 mg), using the dosage specific tooling (e.g. approx. 6 mm, round, curved).

Coating:

Prepare a suspension in water with basic coating premixes black, red, yellow and/or white. Coat the above obtained cores in a perforated coating pan, and dry.

EXAMPLE 9.3

Film-Coated Tablet

Film-coated tablets containing e.g. 50 mg of the mono-fumarate of (R)-3-(6-(4-methylphenyl)-pyridin-3-yloxy)-1-aza-bicyclo[2.2.2]octane may be prepared as follows:

Final Blend:

Weigh-in mono-fumarate of (R)-3-(6-(4-methylphenyl)-pyridin-3-yloxy)-1-aza-bicyclo[2.2.2]octane coarse (e.g. approx. 15.5%), microcrystalline cellulose (e.g. approx. 25%), sprayed lactose (e.g. approx. 53%), sodium-carboxymethylcellulose XL (e.g. approx. 3%) and Aerosil (e.g. approx. 0.5%) and mix in a tumble blender (approx. 100-300 rotations). Pass this mixture through a sieve of approx. 0.5-1.0 mm mesh-size and mix again (approx. 100-300 rotations).

Add the sodium-stearyl-fumarate (e.g. approx. 3%) through a handsieve at approx. 0.5-10 mm and mix in a tumble blender (approx. 30-150 rotations).

Compression:

Compress the above final blend on a rotary press to cores, using the dosage specific tooling (e.g. approx. 15*5.9 mm, round, curved).

Coating:

Prepare a suspension in water with basic coating premixes black, red, yellow and/or white. Coat the above obtained cores in a perforated coating pan, and dry.

EXAMPLE 10

Biological Data

The usefulness of (R)-3-(6-(4-methylphenyl)-pyridin-3-yloxy)-1-aza-bicyclo[2.2.2]octane in its various forms, e.g. in free base form (Compound A) or in mono-fumarate salt form (Compound B) in the treatment of the above-mentioned disorders can be confirmed in a range of standard tests including those indicated below.

10.1. In-vitro Tests: Selectivity of (R)-3-(6-(4-methylphenyl)-pyridin-3-yloxy)-1-aza-bicyclo[2.2.2]octane against α4β2-nAChR Based on the activity/selectivity data shown below it is concluded that said compound is a selective agonist at the α7-nAChR.

| | α7-nAChR activity | | | | |
|---|---|---|---|---|---|
| | Potency $EC_{50}$ | Efficacy compared to epibatidine | α4β2-nAChR activity | | |
| Compound | (nM) | (100%) | $IC_{50}$ (nM) | $EC_{50}$ (nM) | fold selectivity |
| A | 35 | 75 | 5598 | >100'000 | 164 |

Assay:

To assess α7-nAChR activity, a functional assay was employed using GH3 cells that recombinantly expressed human α7-nAChR. 40000 cells per well were seeded 48 h prior to the experiment on black 96-well plates (Costar) and incubated at 37° C. in a humidified atmosphere (5% $CO_2$/95% air). On the day of the experiment, medium was removed by flicking the plates and replaced with 0.1 ml growth medium containing 0.002 mM Fluo-4, (Molecular Probes) in the presence of 2.5 mM probenecid (Sigma). The cells were incubated at 37° C. in a humidified atmosphere (5% $CO_2$/95% air) for 1 h. Plates were flicked to remove excess of Fluo-4, washed twice with Hepes-buffered salt solution (HBSS, in mM: NaCl 130, KCl 5.4, $CaCl_2$ 2, $MgSO_4$ 0.8, $NaH_2PO_4$ 0.9, glucose 25, Hepes 20, pH 7.4; HBS) and refilled with 0.1 ml of HBS containing antagonist when appropriate. The incubation in the presence of the antagonist lasted 3-5 minutes. Plates were placed in the cell plate stage of a FLIPR device (fluorimetric imaging plate reader, Molecular Devices, Sunnyvale, Calif., USA). After recording of the baseline (laser: excitation 488 nm at 1 W, CCD camera opening of 0.4 seconds) the agonists (0.05 ml) were added to the cell plate using the FLIPR 96-tip pipettor while simultaneously recording the fluorescence. Calcium kinetic data were normalized to the maximal fitted response induced by epibatidine, which is a full agonist at α7-nAChR. Four parameter Hill equations were fitted to the concentration-response. Values of Emax (maximal effect in % compared to the epibatidine response) and $EC_{50}$ (concentration producing half the maximal effect in µM) were derived from this fit.

Assay described in: D Feuerbach et al, Neuropharmacology (2005), 48, 215-227.

To assess the activity of the compound of the invention on the human neuronal nAChR α4β2, a similar functional assay is carried out using a human epithelial cell line stably expressing the human α4β2 subtype (Michelmore et al, Naunyn-Schmiedeberg's Arch. Pharmacol. (2002) 366, 235).

10.2. In-Vivo Preclinical Tests

10.2.1. Oral bioavailability and brain penetration of (R)-3-(6-(4-methylphenyl)-pyridin-3-yloxy)-1-azabicyclo[2.2.2]octane in Mice Based on the pharmacokinetic data shown below it is concluded that the brain concentration of said compound in mice is beyond (or at least equal) to the compound's $EC_{50}$ at the α7-nAChR for at least 4 hours following an acute oral dose of 30 µmol/kg of the compound in free base form.

Compound A:

| Administration | Time (hour) | Plasma (pmoles/ml ± SD) | Brain (pmoles/g ± SD) | Ratio Brain/plasma |
|---|---|---|---|---|
| 30 µmol/kg p.o. | 0.25 | 573 ± 234 | 4631 ± 1717 | 8 |
| 30 µmol/kg p.o. | 0.5 | 559 ± 143 | 11430 ± 3441 | 20 |
| 30 µmol/kg p.o. | 1 | 322 ± 135 | 14948 ± 4716 | 46 |
| 30 µmol/kg p.o. | 4 | 20 ± 16 | 1272 ± 715 | 62 |
| 30 µmol/kg p.o. | 8 | 3.4 ± 0.8 | 58 ± 27 | 17 |
| 30 µmol/kg p.o. | 24 | — | — | — |

Assay:

Compounds were orally (30 µmol/kg) administered. Male mice (30-35 g, OF 1/ICstrain) were sacrificed at indicated time points after oral administration. Trunk-blood was collected in EDTA-containing tubes and the brain was removed and immediately frozen on dry ice. To 100 µl plasma 10 µl internal standard (1.0 µmol of a compound with solubility and ionization properties similar to test compounds) was added and extracted three times with 500 µl dichloromethane. The combined extracts were then dried under a stream of nitrogen and re-dissolved in 100 µl acetonitrile/water (70% acetonitrile). Brains were weighed and homogenized in water (1:5 w/v). Two 100 µl aliquots of each homogenate+10 µl of internal standard (same standard as used for the plasma samples) were extracted three times with 500 µl dichloromethane and further processed as the plasma samples. Samples were separated on Beckmann high-performance liquid chromatography equipment system with an autosampler (Gilson 233XL). A 10 min linear gradient (10-70%) of acetonitrile containing 0.5% (v/v) formic acid was used to elute the compounds from Nucleosil CC-125/2 C18 reversed phase (Machery & Nagel) column.

The limit of detection (LOD), defined as the lowest concentration of the extracted standard sample with a signal to noise ratio of ~3.

10.2.2. Functional read-out of (R)-3-(6-(4-methylphenyl)-pyridin-3-yloxy)-1-aza-bicyclo[2.2.2]octane in Mice Social Recognition Test Based on the functional in-vivo data shown below it is concluded that oral dosing of said compound at relevant concentrations leads to a specific effect associated with α7-nAChR (i.e. cognition enhancement in the Social Recognition Test in mouse).

| Compound | Reduction in time scrutinizing in % ± SEM at 24 h | Dose in mg/kg |
|---|---|---|
| A | 36 ± 6 | 0.3 |

Assay:

Social interactions between two experimental animals are influenced by their degree of familiarity: the better they know each other, the less time they spend on mutual scrutiny at each meeting. In agreement with published data in rats (Mondadori et al., 1993) we have observed (i) that an adult mouse shows a shortened scrutiny of a young conspecific if the two mice are brought together again within a short time interval (e.g. 1 hour), (ii) that this curtailment is attributable to memory processes: it does not occur if the familiar young partner is replaced by a strange (unfamiliar) young mouse on the second occasion and (iii) that the adult mouse's recollection of the previously scrutinized juvenile partner fades with the elapsed time, i.e., after 24 h, scrutiny takes just about as long as at the first encounter. Memory enhancing agents (i.e. oxiracetam) facilitate learning to the extent that the previously met (familiar) partner is still remembered after 24 h, whereas in vehicle treated control animals the memory usually fades after less than 1 hour (Thor and Holloway, 1982) or after 2-3 hours.

Baseline-test: Pairs consisting of one adult and one young mouse were assigned at random to the experimental and control groups. In each pair only the adult mouse was orally treated 1 hour before the trial with either vehicle or the test compound. The duration of active contacts of the adult mouse with the young mouse was manually recorded over a period of 3 min, including the following behavioural, approach-related items: sniffing, nosing, grooming, licking, pawing and playing, anogenital exploration and orientation toward the young mouse; orientation, thereby, was defined as tip of nose of the adult mouse less than approximately 1 cm distant from the young mouse's body.

Re-test: Twenty-four hours after the baseline-test, the adults in each treatment group were confronted again with the previously encountered (familiar) partner, whereas the half of the adult animals were put together with the previously encountered (familiar) partner and the other half with another (unfamiliar) young mouse. Again the duration of active approach-behaviours was recorded during a 3-min period. Prior to re-test no oral injection was given. In the table the reduction in time scrutinizing the familiar partner at time 24 compared with the familiar partner at time 0 minutes is given (value of zero would signify no reduction).

10.2.3. Oral bioavailability of (R)-3-(6-(4-methylphenyl)-pyridin-3-yloxy)-1-aza-bicyclo[2.2.2]octane in Dogs Based on the pharmacokinetic data shown below it is concluded that the compound reaches significant blood levels in dogs following an acute oral dose of 1.4 µmol/kg of the compound in fumarate salt form.

Compound B:

| Administration | Time (hour) | Plasma (pmoles/ml ± SD) |
|---|---|---|
| 1.4 μmol/kg p.o. | 0.25 | 14.7 ± 1.1 |
| 1.4 μmol/kg p.o. | 0.5 | 49.4 ± 21.9 |
| 1.4 μmol/kg p.o. | 1 | 67.6 ± 22.6 |
| 1.4 μmol/kg p.o. | 2 | 75.2 ± 36.8 |
| 1.4 μmol/kg p.o. | 4 | 27.5 ± 13.3 |
| 1.4 μmol/kg p.o. | 8 | 8.1 ± 3.0 |
| 1.4 μmol/kg p.o. | 24 | 0.8 ± 0.7 |

Assay:

The compound was given to N=3 male beagle dogs in tritiated form:

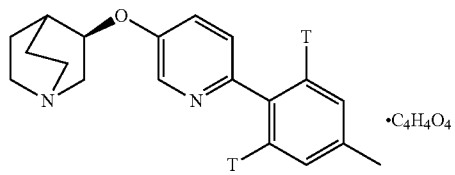

The concentration of the compound in blood was determined by LC-RID. The procedure involved the addition of 5 μg of the compound as internal standard (200 μL of solution containing 25 μg/mL of the compound) to 1 mL of blood. After further addition of 1 mL of water, 0.1 mL of buffer pH 9 and 4 mL of tert-butylmethylether, the samples were shaken for 30 min and centrifuged (4000 g for 10 min at 22° C.). The organic phase was transferred into a tube and evaporated in a Speedvac. The residue was reconstituted in 250 μL of mobile phase-water (80:20 v/v) followed by 75 μL of n-hexane and transferred into an autosampler vial. After centrifugation (13,000 g for 2 min at 22° C.), the hexane layer was pipetted off and discarded, 200 μL of the remainder was injected onto an RP18 column (Waters XTerra, 5 μm, 3.9×150 mm at 40° C.) to separate the compound from potential metabolites and endogenous compounds. The mobile phase of ammonium acetate (10 mM:0.1% v/v TFA-acetonitrile, 58:42 v/v) was used at a flow rate of 1.0 mL/min. The effluent was monitored by a UV-detector set at 261 nm. The peak corresponding to the unchanged compound was collected in a polyethylene vial by a fraction collector (SuperFrac, Pharmacia LKB) and analyzed for radioactivity. The concentration of the compound in each sample was calculated from the ratio of the amount of radioactivity in the eluate fraction to the area of the ultraviolet absorbance of the non-radiolabeled the compound, that was used as the internal standard.

EXAMPLE 10.2.4

Pharmacokinetics of (R)-3-(6-(4-methylphenyl)-pyridin-3-yloxy)-1-aza-bicyclo[2.2.2]octane in Rats Please note that dosing information in this Example 10.2.4 is given relative to the free form, (R)-3-(6-(4-methylphenyl)-pyridin-3-yloxy)-1-aza-bicyclo[2.2.2]octane, and is independent from the salt forming agent. If a salt forming agent is used (e.g. fumarate), a corresponding higher amount of the salt will be used to achieve the intended dosing.

Based on the pharmacokinetic data shown below:
After acute oral dosing of 10 mg/kg (R)-3-(6-(4-methylphenyl)-pyridin-3-yloxy)-1-aza-bicyclo[2.2.2]octane in mono-fumarate salt form, a Cmax of the free form in plasma of 161±53 ng/ml was reached at 0.25-0.5 h. The AUClast amounted to 249±42 h·ng/ml. After acute oral dosing of 10 mg/kg (R)-3-(6-(4-methylphenyl)-pyridin-3-yloxy)-1-aza-bicyclo[2.2.2]octane in free form, a Cmax of the free form in plasma of 112±40 ng/ml was reached at 0.25-0.5 h. The AUClast amounted to 200±62 h·ng/ml.

Pharmacokinetics of (R)-3-(6-(4-methylphenyl)-pyridin-3-yloxy)-1-aza-bicyclo[2.2.2]octane in Wistar rats after oral administration of 10 mg/kg of the compound in mono-fumarate salt form (Compound B) and in free base form (Compound A) were assessed.

Both compounds were dissolved in Klucel™ (0.5% in water) and were orally administered by gavage (5 ml/kg) to conscious rats (n=8, cross-over design).

K3-EDTA blood (~0.2 ml) was collected by puncture of a sublingual vein under light isoflurane anesthesia at the following time points: 0.25, 0.5, 1, 2, 3, 4, 6, 8, 24 h post dose. Immediately after sampling, blood samples were put on ice and were processed to plasma by centrifugation at 4° C. within 15 min after sampling (1000 g, 10 min, 4° C.) to obtain ~100 μl plasma/sample. All plasma samples were stored at −80° C. until analysis. Since the PK study was performed in a cross-over design, a recovery period of approximately 2 weeks took place before the next treatment/blood sampling was performed.

The determination of compounds in plasma was done by LC-MS/MS using electrospray ionization.

a. Concentrations (nq/ml) and derived pharmacokinetic parameters of (R)-3-(6-(4-methylphenyl)-pyridin-3-yloxy)-1-aza-bicyclo[2.2.2]octane in plasma of male Wistar rats following oral administration of 10 mg/kg free base

| | Phase | | | | | | |
|---|---|---|---|---|---|---|---|
| | 1 Rat 01 | 1 Rat 02 | 1 Rat 03 | 1 Rat 04 | 2 Rat 05 | 2 Rat 06 | 2 Rat 07 |
| Time (h) | | | | | | | |
| 0.25 | 58.8 | 89.6 | 83.0 | 79.4 | 105 | 188 | 49.0 |
| 0.5 | 34.8 | 51.2 | 64.5 | 94.8 | 119 | 122 | 117 |
| 1 | 20.1 | 31.4 | 63.9 | 36.0 | 65.8 | 83.6 | 87.0 |
| 2 | 6.9 | 12.6 | 51.7 | 16.2 | 43.2 | 46.9 | 42.2 |
| 3 | 5.31 | 8.38 | 26.3 | 7.84 | 23.0 | 34.4 | 18.4 |
| 4 | 3.94 | 3.99 | 18.2 | 4.54 | 8.63 | 21.1 | 13.8 |
| 6 | 4.87 | 1.81 | 6.62 | 1.27 | 5.32 | 4.38 | 4.59 |
| 8 | 6.62 | 0.812 | 2.46 | 1.32 | 3.67 | 1.54 | 2.25 |
| 24 | 1.40 | 2.44 | 0.547 | 1.02 | 0* | 0.632 | 0.248 | a. Concentrations (nq/ml) and derived pharmacokinetic parameters of (R)-3-(6-(4-methylphenyl)-pyridin-3-yloxy)-1-aza-bicyclo[2.2.2]octane in plasma of male Wistar rats following oral administration of 10 mg/kg free base

| | | | | | | | |
|---|---|---|---|---|---|---|---|
| Body weight (kg)[b] | 0.297 | 0.277 | 0.288 | 0.271 | 0.309 | 0.318 | 0.315 |
| Dose (mg/kg) | 10.1 | 10.2 | 9.76 | 10.1 | 9.88 | 9.96 | 10.0 |
| Tmax (h) | 0.25 | 0.25 | 0.25 | 0.50 | 0.50 | 0.25 | 0.50 |
| Tlast (h) | 24.0 | 24.0 | 24.0 | 24.0 | 8.0 | 24.0 | 24.0 |
| Cmax (ng/mL) | 58.8 | 89.6 | 83.0 | 94.8 | 119 | 188 | 117 |
| Cmax/Dose (ng/mL)/(mg/kg) | 5.81 | 8.79 | 8.50 | 9.40 | 12.0 | 18.9 | 11.7 |
| AUClast (h·ng/mL) | 141 | 123 | 238 | 136 | 214 | 296 | 234 |
| AUClast/Dose (h·ng/mL)/(mg/kg) | 14.0 | 12.0 | 24.4 | 13.5 | 21.6 | 29.7 | 23.4 |
| T1/2 (h) | 8.67 | nd | 5.71 | nd | 3.24 | nd | 4.54 |
| T1/2 range (h) | [6-24] | nd | [6-24] | nd | [4-8] | nd | [6-24] |

| | Phase 2 Rat 08 | Mean All | SD All | CV (%) |
|---|---|---|---|---|
| Time (h) | | | | |
| 0.25 | 145 | 100 | 46.2 | 46.3 |
| 0.5 | 65.0 | 83.5 | 34.0 | 40.7 |
| 1 | 33.8 | 52.7 | 25.6 | 48.5 |
| 2 | 29.9 | 31.2 | 17.3 | 55.5 |
| 3 | 6.20 | 16.2 | 10.9 | 67.3 |
| 4 | 8.55 | 10.3 | 6.66 | 64.4 |
| 6 | 6.06 | 4.37 | 1.90 | 43.5 |
| 8 | 9.67 | 3.54 | 3.08 | 86.9 |
| 24 | 0.287 | 0.822 | 0.792 | 96.4 |
| Body weight (kg)[b] | 0.350 | — | — | — |
| Dose (mg/kg) | 9.65 | 10.0 | 0.184 | 1.85 |
| Tmax (h) | 0.25 | 0.25 [0.25-0.50][a] | | |
| Tlast (h) | 24.0 | 24.0 [8.0-24.0][a] | | |
| Cmax (ng/mL) | 145 | 112 | 40.4 | 36.1 |
| Cmax/Dose (ng/mL)/(mg/kg) | 15.0 | 11.3 | 4.14 | 36.7 |
| AUClast (h·ng/mL) | 236 | 200 | 61.9 | 30.6 |
| AUClast/Dose (h·ng/mL)/(mg/kg) | 24.5 | 20.4 | 6.43 | 31.5 |
| T1/2 (h) | 3.67 | 5.17 | 2.17 | 42.1 |
| T1/2 range (h) | [6-24] | | | |

[a]Median [range]
[b]At time of treatment
nd: Not determined due to $r^2 < 0.75$ or AUC % extrapolated > 30%
*Values BLOQ (0.150 ng/mL) were set to 0 for Phoenix PK calculations.

b. Concentrations (ng/ml) and derived pharmacokinetic parameters of (R)-3-(6-(4-methylphenyl)-pyridin-3-yloxy)-1-aza-bicyclo[2.2.2]octane in plasma of male Wistar rats following oral administration of 10 mg/kg mono-fumarate.

| | Phase | | | | | | |
|---|---|---|---|---|---|---|---|
| | 2 Rat 01 | 2 Rat 02 | 2 Rat 03 | 2 Rat 04 | 1 Rat 05 | 1 Rat 06 | 1 Rat 07 |
| Time (h) | | | | | | | |
| 0.25 | 167 | 162 | 77.8 | 89.0 | 242 | 204 | 93.3 |
| 0.5 | 104 | 130 | 78.4 | 99.7 | 143 | 179 | 184 |
| 1 | 67.1 | 88.8 | 41.3 | 62.8 | 83.2 | 80.8 | 101 |
| 2 | 27.4 | 39.2 | 37.8 | 24.6 | 47.1 | 37.6 | 54.8 |
| 3 | 12.4 | 17.7 | 25.3 | 11.7 | 19.6 | 20.6 | 25.1 |
| 4 | 9.06 | 10.6 | 13.3 | 5.90 | 9.71 | 11.8 | 13.0 |
| 6 | 7.49 | 3.47 | 7.63 | 5.79 | 4.29 | 4.24 | 4.05 |
| 8 | 2.91 | 2.35 | 3.62 | 2.62 | 2.46 | 1.94 | 2.38 |
| 24 | 0* | 0.276 | 0.210 | 0.169 | 0* | 1.40 | 0.162 |
| Body weight (kg)[b] | 0.341 | 0.315 | 0.330 | 0.300 | 0.268 | 0.266 | 0.276 |
| Dose (mg/kg) | 9.73 | 9.86 | 9.95 | 9.82 | 9.61 | 9.69 | 10.1 |
| Tmax (h) | 0.25 | 0.25 | 0.50 | 0.50 | 0.25 | 0.25 | 0.50 |
| Tlast (h) | 8.0 | 24.0 | 24.0 | 24.0 | 8.0 | 24.0 | 24.0 |

-continued b. Concentrations (ng/ml) and derived pharmacokinetic parameters of (R)-3-(6-(4-methylphenyl)-pyridin-3-yloxy)-1-aza-bicyclo[2.2.2]octane in plasma of male Wistar rats following oral administration of 10 mg/kg mono-fumarate.

| | | | | | | | |
|---|---|---|---|---|---|---|---|
| Cmax (ng/mL) | 167 | 162 | 78.4 | 99.7 | 242 | 204 | 184 |
| Cmax/D (ng/mL)/(mg/kg) | 17.2 | 16.4 | 7.88 | 10.2 | 25.2 | 21.1 | 18.3 |
| AUClast (h·ng/mL) | 202 | 259 | 212 | 188 | 269 | 292 | 298 |
| AUClast/D (h·ng/mL)/(mg/kg) | 20.8 | 26.3 | 21.4 | 19.2 | 28.0 | 30.1 | 29.6 |
| T1/2 (h) | 2.44 | 5.02 | 3.62 | 3.71 | 2.02 | nd | 3.97 |
| T1/2 range (h) | [4-8] | [6-24] | [6-24] | [6-24] | [4-8] | nd | [6-24] |

| | Phase 1 Rat 08 | Mean All | SD All | CV (%) |
|---|---|---|---|---|
| Time (h) | | | | |
| 0.25 | 153 | 149 | 58.5 | 39.4 |
| 0.5 | 138 | 132 | 37.4 | 28.3 |
| 1 | 94.2 | 77.4 | 19.4 | 25.1 |
| 2 | 42.6 | 38.9 | 9.81 | 25.2 |
| 3 | 23.2 | 19.5 | 5.27 | 27.1 |
| 4 | 11.1 | 10.6 | 2.39 | 22.6 |
| 6 | 3.87 | 5.10 | 1.66 | 32.5 |
| 8 | 2.07 | 2.54 | 0.529 | 20.8 |
| 24 | 0.344 | 0.320 | 0.453 | 141 |
| Body weight (kg)[b] | 0.290 | — | — | — |
| Dose (mg/kg) | 9.77 | 9.81 | 0.146 | 1.49 |
| Tmax (h) | 0.25 | | 0.25 [0.25-0.50][a] | |
| Tlast (h) | 24.0 | | 24.0 [8.0-24.0][a] | |
| Cmax (ng/mL) | 153 | 161 | 52.9 | 32.8 |
| Cmax/D (ng/mL)/(mg/kg) | 15.7 | 16.5 | 5.54 | 33.6 |
| AUClast (h·ng/mL) | 272 | 249 | 42.2 | 16.9 |
| AUClast/D (h·ng/mL)/(mg/kg) | 27.9 | 25.4 | 4.30 | 16.9 |
| T1/2 (h) | 5.51 | 3.76 | 1.26 | 40.3 |
| T1/2 range (h) | [6-24] | | | |

[a]Median [range]
[b]At time of treatment
nd: Not determined due to $r^2 < 0.75$.
*Values BLOQ (0.150 ng/mL) were set to 0 for Phoenix PK calculations.

EXAMPLE 11

Preparation of 5-chloro-2-(4-methylphenyl)pyridine (Process according to Section A)

Under nitrogen 2,5-dichloro-pyridine (40 g, 270 mmol), 4-methylphenylboronic acid (39 g, 289 mmol) and bistriphenylphosphin-palladium(II) dichloride (1.14 g; 1.6 mmol) were suspended in water (258 g)/THF (117 g) for approx. 30 min at 35-55° C. A solution of tripotassium phosphate (143.4 g, 676 mmol) in water (143 g) was added at 35-55° C. during approx. 60-120 min and 55° C. was maintained for another approx. 30-45 min. More tripotassium phosphate (22.9 g, 108 mmol) in water (22.9 g) was added over a period of approx. 30 min and the temperature was raised to 55-60° C. to complete the reaction within another approx. 2 h.

For extractive palladium removal a solution of cysteine (ca. 16 g) in water (115 g) was added to the reaction mixture at 60-55° C. After approx. 1 h at 55° C. the biphasic reaction mixture was clarified by filtration over a pad of cellflock filter aid (2-5 g) and a THF/water mixture (110 g/75 g) was used for rinsing. The layers of the combined filtrates were separated at 25° C. and the salt containing water layer was extracted with THF (1×57 g). The combined THF layers were diluted with ethanol 94% (195 g) and concentrated by distillation under reduced pressure (300-200 mbar) at a jacket temperature of 45° C. in order to remove the bulk of THF (175-250 g). To the remaining product solution further ethanol (97 g) was added and at 45-55° C. water (565 g) was gradually added over a period of approx. 60 min to induce and maintain crystallization. After 30 min the temperature was lowered to approx. 20° C. in approx. 90-120 min and after another hour at that temperature the solids were collected by filtration, washed with ethanol/water 1:2 and dried under reduced pressure to yield 5-chloro-2-(4-methylphenyl)pyridine (52.5 g; 95% of theory; purity>95%; Pd <25 ppm).

EXAMPLE 12

Preparation of (R)-3-(6-(4-methylphenyl)-pyridin-3-yloxy)-1-aza-bicyclo[2.2.2]octane in free form and fumarate salt form (Process according to Section B)

EXAMPLE 12.1

Formation of Free Form

Under nitrogen, to 3R-quinuclidinol (43.8 g, 0.34 mol) in DMSO (792 g) an approx. 20% THF solution of potassium tert-butoxide (210 g, 0.375 mol) was added and at approx. 40-45° C. under reduced pressure the THF solvent was distilled off. The temperature of the reaction mixture was raised to 90° C. and the solid 5-chloro-2-(4-methylphenyl)pyridine (61.2 g, 0.30 mol) was gradually added in at least 4 portions.

The temperature was raised further to approx. 100-105° C. and after at least another 3 hours at this temperature the reaction to (R)-3-(6-(4-methylphenyl)-pyridin-3-yloxy)-1-aza-bicyclo[2.2.2]octane was complete.

Water (150 g) was added to the reaction mixture at 60-25° C. and the temperature was gradually lowered to approx. 20° C. in approx. 60 min and additional water (210 g) was added. After at least another 2 further hours at this temperature the fine solids were collected by filtration, washed successively with DMSO/water (approx. 322 g; 2:1 mixture), water (500 g) and water/ethanol (approx. 500 g; 9:1 mixture) and dried at 60° C. under reduced pressure to yield (R)-3-(6-(4-methylphenyl)-pyridin-3-yloxy)-1-aza-bicyclo[2.2.2]octane (56.3 g, 63% of theory).

EXAMPLE 12.2

Formation of Fumarate Salt Form

To a clear solution of (R)-3-(6-(4-methylphenyl)-pyridin-3-yloxy)-1-aza-bicyclo[2.2.2]octane (39.6 g; 0.135 mol) and fumaric acid (16.4 g, 0.141 mol) in ethanol (330 g)/water (21 g) at 65° C. tert.-butylmethylether (142.5 g) was added and the reaction mixture was cooled to 23° C. in approx. 60 min. Further tert.-butylmethylether (170.6 g) was added. After at least another 2 hours the solids were collected by filtration, washed with ethanol/tert.butylmethylether (153 g; 1.1 mixture) and dried at 55-60° C. under reduced pressure to yield (R)-3-(6-(4-methylphenyl)-pyridin-3-yloxy)-1-aza-bicyclo[2.2.2]octane hydrogenfumarate (43.8 g, 79% of theory).

EXAMPLE 13

Preparation of (R)-3-(6-(4-methylphenyl)-pyridin-3-yloxy)-1-aza-bicyclo[2.2.2]octane in free form and fumarate salt form (Process according to Section B1)

EXAMPLE 13.1

Formation of Free Form

Under nitrogen to 3R-quinuclidinol (41.4 g, 0.325 mol) in DMSO (320 g) a solution of 5-chloro-2-(4-methylphenyl)pyridine (51 g, 0.250 mol) in toluene (201 g) was added. The temperature was raised gradually to approx. 100-105° C. while residual water, if any, was removed by refluxing under reduced pressure at a water trap for ca. 45 min. Over a period of approx. 90 min an approx. 20% THF solution of potassium tert-butoxide (158.8 g, 0.283 mol) was continuously added while gradually the THF solvent distilled off. After another 2-5 hours at approx. 100-105° C. the reaction to (R)-3-(6-(4-methylphenyl)-pyridin-3-yloxy)-1-aza-bicyclo[2.2.2]octane was complete.

Water (293 g) was added to the reaction mixture at 60-25° C. The layers were separated and the toluene layer was washed with water (2×42 g). The toluene solution was dried at ca. 60° C. by refluxing under reduced pressure at a water trap for ca. 45-60 min.

EXAMPLE 13.2

Formation of Fumarate Salt Form

To the toluene solution of Example 13.1, at ca. 50-55° C., a slurry of fumaric acid (26.1 g, 0.9 eq) in EtOH 94% (22 g) and toluene (97 g) was gradually added. Further toluene (97 g) was added for rinsing and after another ca. 30-60 min at 55° C. the temperature was gradually lowered to approx. 20° C. in approx. 120-180 min. After at least another 1 hour the solids were collected by filtration, washed with water saturated toluene (2×104 g) and dried at 60° C. under reduced pressure to yield (R)-3-(6-(4-methylphenyl)-pyridin-3-yloxy)-1-aza-bicyclo[2.2.2]octane hydrogenfumarate (84.8 g; 82% of theory, based on amount of 5-chloro-2-(4-methylphenyl)pyridine used in Example 13.1).

BRIEF DESCRIPTION OF THE DRAWINGS

FIG. 1 shows the XRPD pattern for the mono-fumarate salt of (R)-3-(6-(4-methylphenyl)-pyridin-3-yloxy)-1-aza-bicyclo[2.2.2]octane in crystalline form FIG. 2 shows the XRPD pattern for the mono-maleate salt of (R)-3-(6-(4-methylphenyl)-pyridin-3-yloxy)-1-aza-bicyclo[2.2.2]octane in crystalline form FIG. 3 shows the XRPD pattern for the mono-hydrochloride salt of (R)-3-(6-(4-methylphenyl)-pyridin-3-yloxy)-1-aza-bicyclo[2.2.2]octane in crystalline form FIGS. 4A, 4B and 4C show the XRPD patterns for Form A, B and C of the phosphate salt of (R)-3-(6-(4-methylphenyl)-pyridin-3-yloxy)-1-aza-bicyclo[2.2.2]octane in crystalline form FIGS. 5A and 5B show the XRPD patterns for Form A and B of the mono-succinate salt of (R)-3-(6-(4-methylphenyl)-pyridin-3-yloxy)-1-aza-bicyclo[2.2.2]octane in crystalline form FIG. 6 shows the XRPD pattern for the mono-malonate salt of (R)-3-(6-(4-methylphenyl)-pyridin-3-yloxy)-1-aza-bicyclo[2.2.2]octane in crystalline form FIGS. 7A and 7B show the XRPD patterns for Form A and B of the free base of (R)-3-(6-(4-methylphenyl)-pyridin-3-yloxy)-1-aza-bicyclo[2.2.2]octane in crystalline form

The invention claimed is:

1. A pharmaceutical composition, which comprises
   a salt of (R)-3-(6-(4-methylphenyl)-pyridin-3-yloxy)-1-aza-bicyclo[2.2.2]octane, wherein said salt is the fumarate, maleate, chloride, phosphate, succinate or malonate salt of (R)-3-(6-(4-methylphenyl)-pyridin-3-yloxy)-1-aza-bicyclo[2.2.2]octane as active ingredient; and
   at least one pharmaceutically acceptable carrier.

2. The pharmaceutical composition of claim 1, further comprising one or more further therapeutic agents as active ingredients and at least one pharmaceutically acceptable carrier.

3. The pharmaceutical composition of claim 1, wherein the salt further comprises mono-fumarate of (R)-3-(6-(4-methylphenyl)-pyridin-3-yloxy)-1-aza-bicyclo[2.2.2]octane.

4. The pharmaceutical composition of claim 3 in the form of a tablet comprising
   (a) a filler;
   (b) a disintegrant;
   (c) a lubricant; and
   (d) a gliding agent,
   wherein the only lubricant present is a lubricant selected from sodium stearyl fumarate, sodium lauryl sulfate, glyceryl behenates, hydrogenated vegetable oils, wax cetyl esters and talc.

5. The pharmaceutical composition of claim 3 in the form of a tablet comprising
   (a) up to 10% by weight mono-fumarate of (R)-3-(6-(4-methylphenyl)-pyridin-3-yloxy)-1-aza-bicyclo[2.2.2]octane as active ingredient;

(b) from 1 to 20% by weight maize starch; from 15 to 35% by weight microcrystalline cellulose; and from 40 to 75% by weight sprayed lactose;
(c) from 0.5 to 5% by weight sodium carboxymethylcellulose XL;
(d) from 0.5 to 3% by weight sodium stearyl fumarate; and
(e) from 0.1 to 1% by weight Aerosil.

6. The pharmaceutical composition of claim 3 in the form of a tablet comprising from 1 to 10% by weight mono-fumarate of (R)-3-(6-(4-methylphenyl)-pyridin-3-yloxy)-1-aza-bicyclo[2.2.2]octane;
wherein the composition comprises an active ingredient layer comprising the mono-fumarate and an auxiliary layer being devoid of the mono-fumarate;
wherein the weight ratio of the active ingredient layer to the auxiliary layer is from 10:90 to 90:10.

7. The pharmaceutical composition of claim 3 in the form of a tablet comprising from 1 to 10% by weight mono-fumarate of (R)-3-(6-(4-methylphenyl)-pyridin-3-yloxy)-1-aza-bicyclo[2.2.2]octane;
wherein the composition comprises an active ingredient layer comprising the mono-fumarate and an auxiliary layer being devoid of the mono-fumarate;
wherein the weight ratio of the active ingredient layer to the auxiliary layer is from 10:90 to 90:10;
wherein the active ingredient layer comprises
(1a) from 11 to 25% by weight of the active ingredient layer the mono-fumarate of (R)-3-(6-(4-methylphenyl)-pyridin-3-yloxy)-1-aza-bicyclo[2.2.2]octane;
(1b) from 15 to 35% by weight of the active ingredient layer microcrystalline cellulose; and from 40 to 70% by weight of the active ingredient layer sprayed lactose;
(1c) from 1 to 5% by weight of the active ingredient layer sodium carboxymethylcellulose XL;
(1d) from 1 to 5% by weight of the active ingredient layer sodium stearyl fumarate; and
(1e) from 0.1 to 1% by weight of the active ingredient layer Aerosil; and
wherein the auxiliary layer comprises
(2a) from 10 to 35% by weight of the auxiliary layer microcrystalline cellulose; and from 50 to 75% by weight of the auxiliary layer sprayed lactose;
(2b) from 1 to 3% by weight of the auxiliary layer sodium carboxymethylcellulose XL;
(2c) from 1 to 5% by weight of the auxiliary layer sodium stearyl fumarate; and
(2d) from 0.1 to 1% by weight of the auxiliary layer Aerosil.

8. The pharmaceutical composition of claim 1, comprising at least 90 weight % of salt, based on the weight of the composition.

9. The pharmaceutical composition of claim 3, wherein the composition is in the form of a tablet.

10. A pharmaceutical composition, which comprises a fumarate salt of (R)-3-(6-(4-methylphenyl)-pyridin-3-yloxy)-1-aza-bicyclo[2.2.2]octane as active ingredient and at least one pharmaceutically acceptable carrier.

11. The pharmaceutical composition of claim 10, wherein the fumarate salt of (R)-3-(6-(4-methylphenyl)-pyridin-3-yloxy)-1-aza-bicyclo[2.2.2]octane is mono-fumarate of (R)-3-(6-(4-methylphenyl)-pyridin-3-yloxy)-1-aza-bicyclo[2.2.2]octane.

12. The pharmaceutical composition of claim 10, further comprising one or more further therapeutic agents as active ingredients.

13. The pharmaceutical composition of claim 10, comprising at least 90 weight % of the fumarate salt of (R)-3-(6-(4-methylphenyl)-pyridin-3-yloxy)-1-aza-bicyclo[2.2.2]octane, based on the weight of the composition.

14. A pharmaceutical composition, which comprises mono-fumarate of (R)-3-(6-(4-methylphenyl)-pyridin-3-yloxy)-1-aza-bicyclo[2.2.2]octane as active ingredient and at least one pharmaceutically acceptable carrier.

15. The pharmaceutical composition of claim 14, further comprising one or more further therapeutic agents as active ingredients.

16. The pharmaceutical composition of claim 14, comprising at least 90 weight % of mono-fumarate of (R)-3-(6-(4-methylphenyl)-pyridin-3-yloxy)-1-aza-bicyclo[2.2.2]octane, based on the weight of the composition.

* * * * *